United States Patent

Davison et al.

[11] Patent Number: 5,322,055
[45] Date of Patent: Jun. 21, 1994

[54] CLAMP COAGULATOR/CUTTING SYSTEM FOR ULTRASONIC SURGICAL INSTRUMENTS

[75] Inventors: Thomas W. Davison, North Attleboro; Stephen DiMatteo, Seekonk, both of Mass.; Paul Smith, West Warwick, R.I.; Gary Whipple, South Attleboro, Mass.

[73] Assignee: Ultracision, Inc., Smithfield, R.I.

[21] Appl. No.: 8,809

[22] Filed: Jan. 27, 1993

[51] Int. Cl.$^5$ ............................................. A61B 17/32
[52] U.S. Cl. ............................................ 601/2; 604/22; 606/169; 606/170; 606/171
[58] Field of Search ................. 128/24 AA; 604/22; 606/37, 39, 40, 45, 46, 52, 169-171, 174, 128

[56] References Cited

U.S. PATENT DOCUMENTS

| | | |
|---|---|---|
| 2,714,890 | 8/1955 | Vang . |
| 3,526,219 | 9/1970 | Balamuth . |
| 3,636,943 | 1/1972 | Balamuth . |
| 3,752,161 | 8/1973 | Bent ........................ 606/169 |
| 3,862,630 | 1/1975 | Balamuth . |
| 3,899,829 | 8/1975 | Storm et al. ............. 606/169 |
| 4,491,132 | 1/1985 | Aikins . |
| 4,497,320 | 2/1985 | Nicholson et al. . |
| 4,674,500 | 6/1987 | DeSatnick . |
| 4,733,662 | 3/1988 | DeSatnick et al. ........... 606/171 |
| 4,877,026 | 10/1989 | de Laforcade ................. 604/22 |
| 5,057,199 | 10/1991 | Lievens et al. . |
| 5,059,210 | 10/1991 | Clark et al. . |
| 5,123,903 | 6/1992 | Quaid et al. . |
| 5,147,357 | 9/1992 | Rose et al. ..................... 606/52 |
| 5,217,460 | 6/1993 | Knoepfler ..................... 606/52 |

Primary Examiner—Lee S. Cohen
Assistant Examiner—K. M. Pfaffle
Attorney, Agent, or Firm—Nixon & Vanderhye

[57] ABSTRACT

An ultrasonic surgical apparatus includes a surgical instrument having a handpiece with a transducer for converting an electrical signal into longitudinal vibratory motion of a blade connected to the handpiece and an accessory releasably connected to the handpiece to enable clamping of tissue against the vibrating blade to afford improved coagulating and cutting of tissue. Scissors-like grips actuate a pivoted clamp jaw along one side of the ultrasonically vibrating blade to compress and bias tissue against the blade in a direction normal to the direction of longitudinal vibratory movement. The clamp jaw and blade are rotatable relative to one another to align a selected blade edge of a multi-edged blade with the clamp jaw for cutting and coagulating while clamping or circumferentially spacing a selected blade edge from the clamp jaw for cutting and coagulating without clamping.

42 Claims, 8 Drawing Sheets

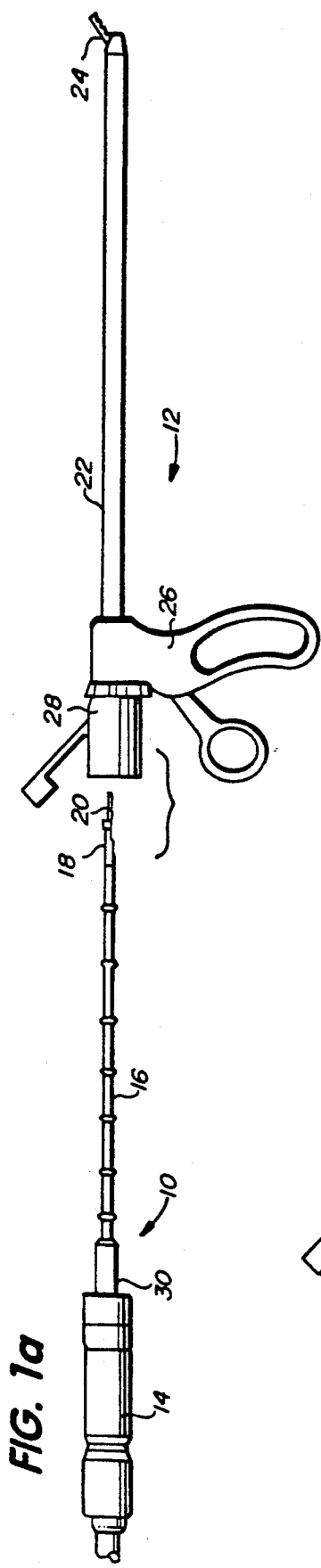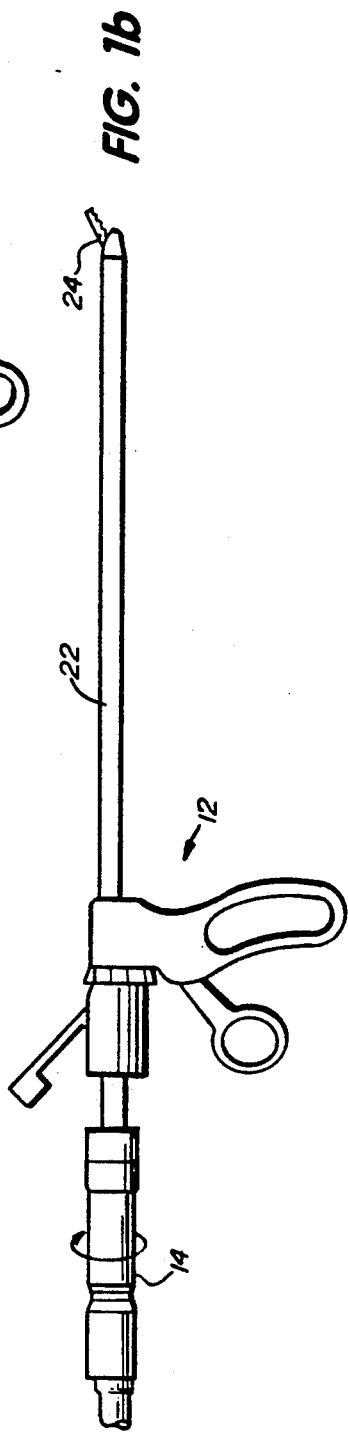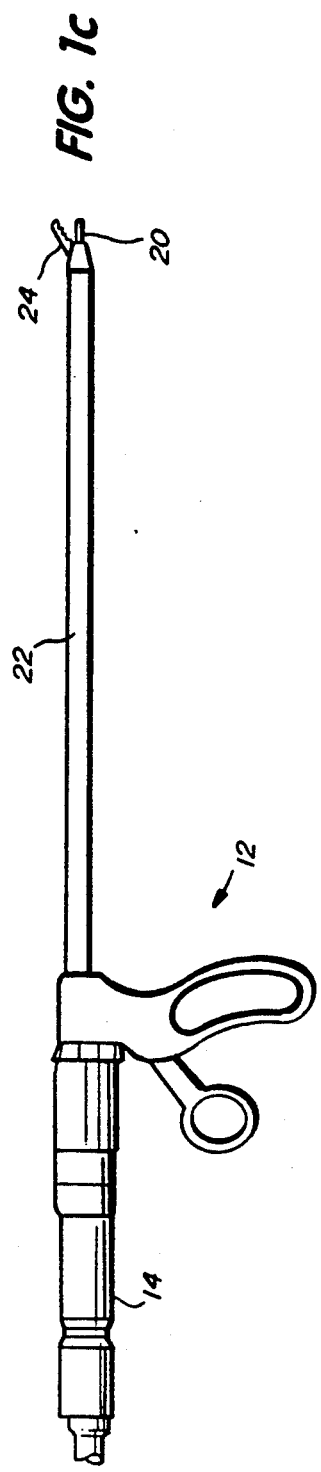

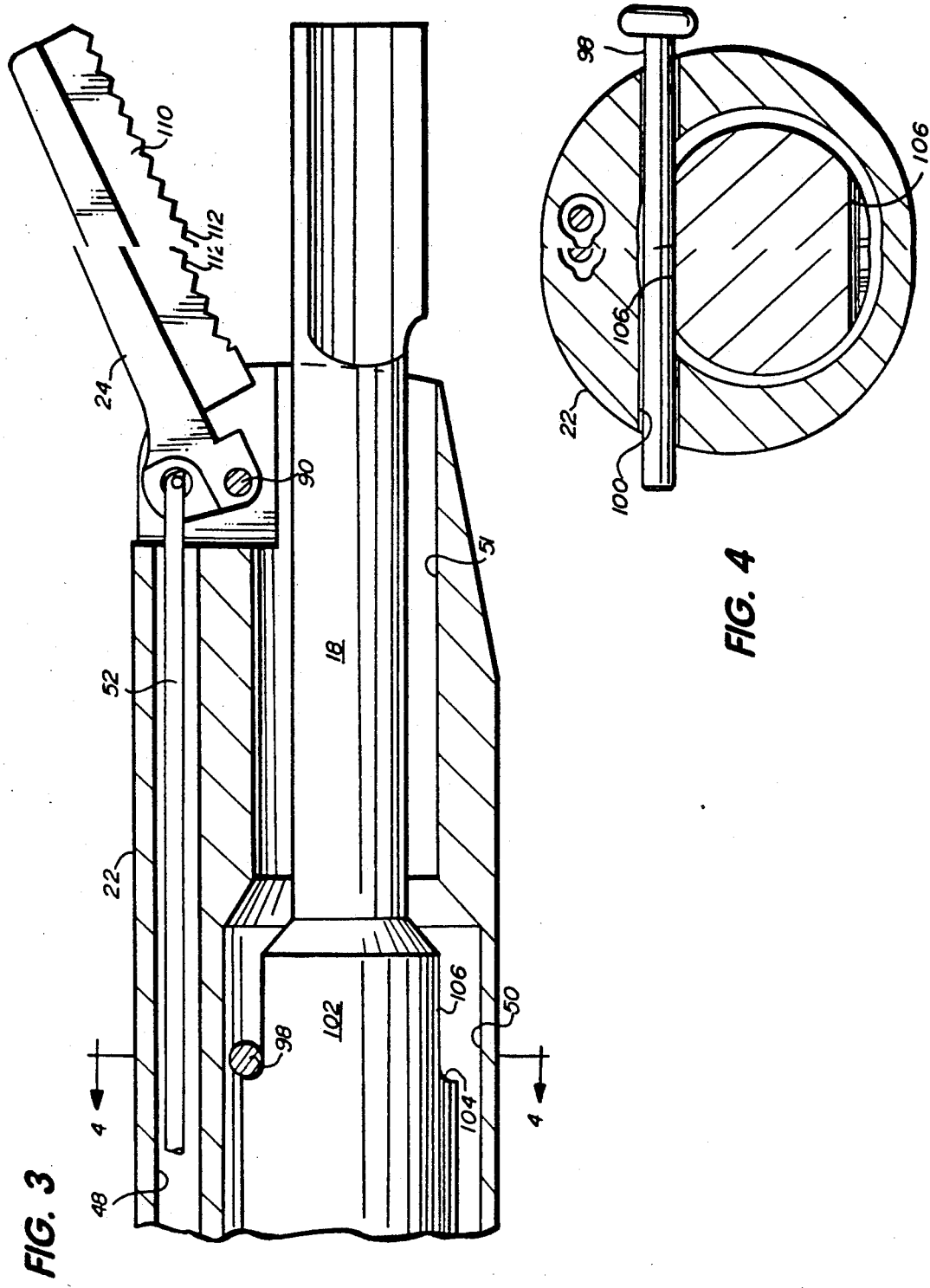

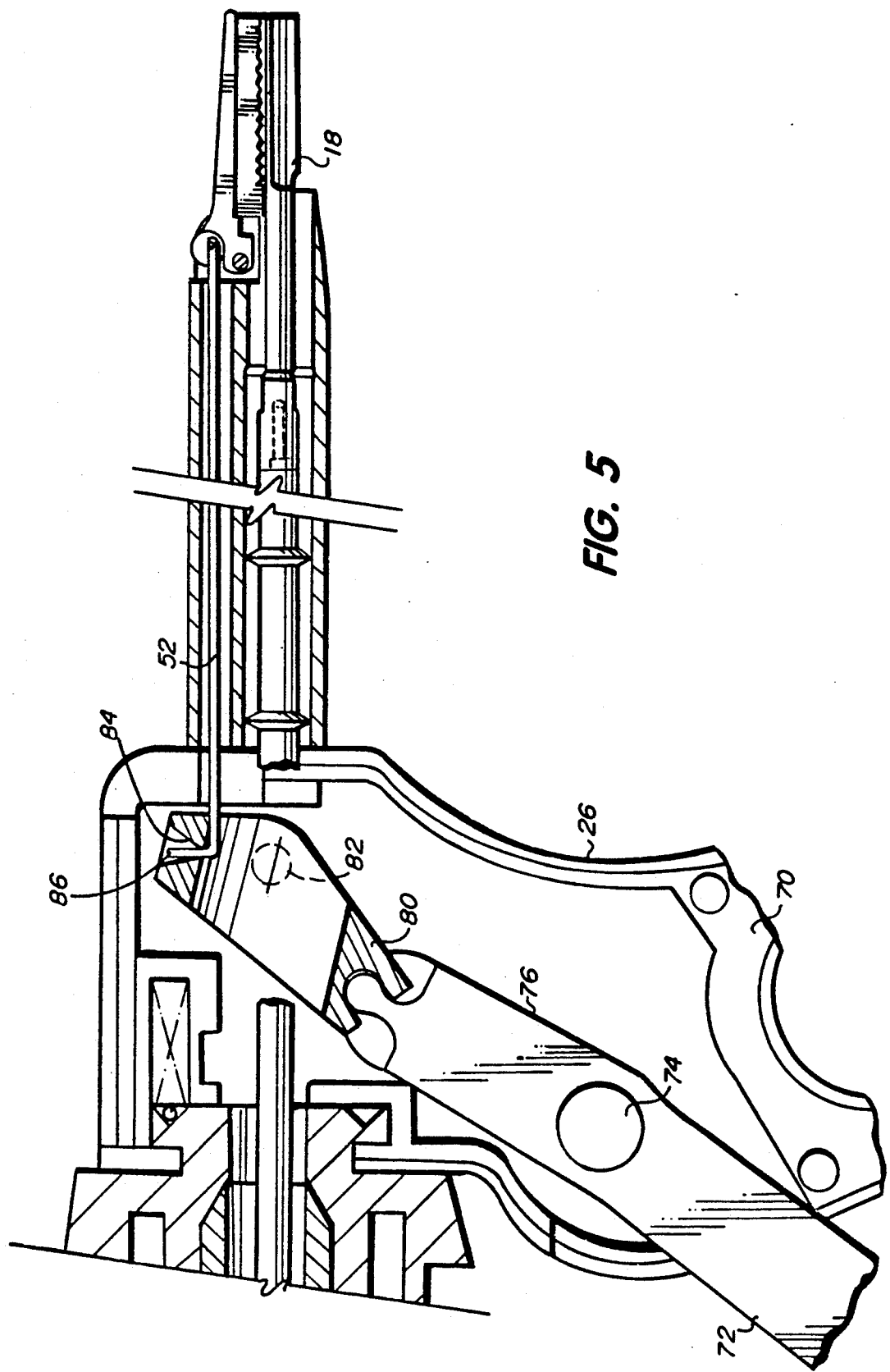

FIG. 9
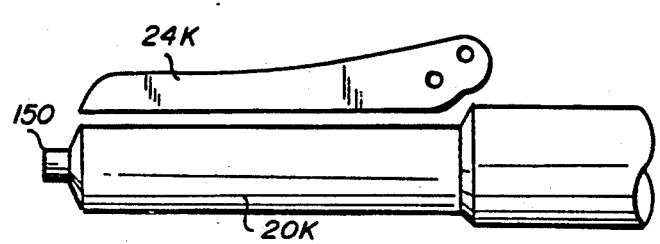
FIG. 8k
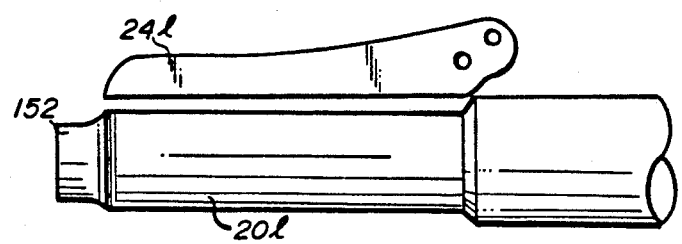
FIG. 8L
FIG. 10
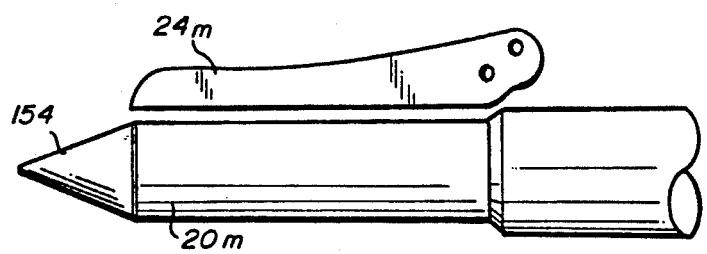
FIG. 8m
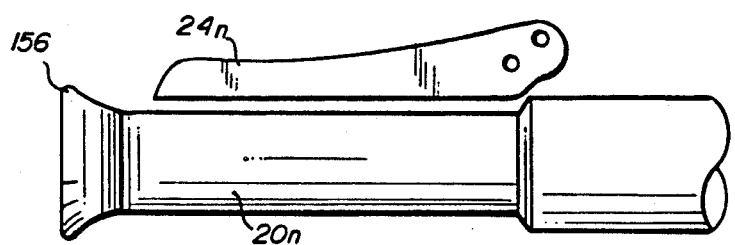
FIG. 8n
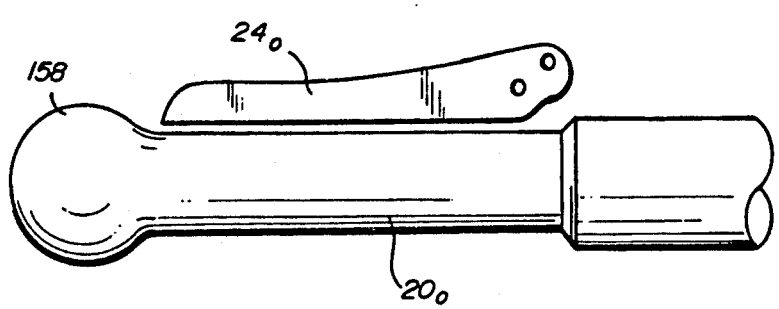
FIG. 8o

CLAMP COAGULATOR/CUTTING SYSTEM FOR ULTRASONIC SURGICAL INSTRUMENTS

TECHNICAL FIELD

The present invention relates to an ultrasonic surgical instrument for cutting, coagulating, grasping and blunt-dissecting tissue and particularly relates to an ultrasonic surgical instrument having a clamp for pressing or biasing tissue against an ultrasonically vibrating blade for improved cutting and coagulation. The present instrument is, in one embodiment, specifically adapted for endoscopic (laparoscopic) surgery, although it has other surgical applications.

BACKGROUND

Ultrasonic vibrating surgical instruments for cutting and coagulating tissue have been disclosed previously in many publications, for example, see U.S. Pat. No. 2,714,890. The benefits from these ultrasonically-operated instruments include enhanced cutting speed, simultaneous hemostasis and cutting, freedom from electrical hazards and smoke, and less build-up of eschar and other material on the blade. To our knowledge, and with one exception, prior ultrasonic surgical devices require the operator to press the ultrasonically vibrating blade directly against the tissue with sufficient pressure to effectively couple ultrasonic energy to that tissue. An example of such device is described and illustrated in prior U.S. patent applications Ser. Nos. 07/670,186, filed Mar. 15, 1991 and 07/828,697, filed Feb. 3, 1992, of common assignee herewith. In both applications, the disclosed ultrasonic surgical device uses an ultrasonically-vibrated surgical blade to cut and coagulate. In those particular disclosures, the ultrasonic surgical instrument is adapted for endoscopic use and, in both cases, employs a handpiece which carries the ultrasonic power generating element, a blade coupler for mounting a surgical blade, and a blade coupler extension, i.e., a solid shaft, interconnecting the handpiece and the blade coupler for transmitting ultrasonic energy from the power source through the blade coupler extension to the blade coupler and blade. The blade coupler extension is disposed in an extension tube and is provided in lengths in integer multiples of the half-wavelength of axial vibration at the frequency of the ultrasonic energy generated by the power source. Isolation mounts are employed along the blade coupler extension at positions of minimal axial ultrasonic activity or nodes to avoid dissipation or damping out of the ultrasonic energy transmitted from the power source to the blade. The disclosures of these two applications are incorporated herein by reference.

While such instruments as disclosed in those two applications have been found eminently satisfactory, there are limitations with respect to their use, as well as the use of other ultrasonic surgical instruments. For example, prior ultrasonic surgical devices, including those of the two prior applications, have limited ability to apply blade-to-tissue pressure when the tissue is soft and loosely supported. Substantial pressure is necessary to effectively couple ultrasonic energy to the tissue. This inability to grasp the tissue results in a further inability to full coapt tissue surfaces while applying ultrasonic energy, leading to less-than-desired hemostasis and tissue joining.

The use of a clamp mechanism to press tissue against an ultrasonic blade can overcome these deficiencies. A clamp mechanism disclosed as useful in an ultrasonic surgical device has been described in U.S. Pat. Nos. 3,636,943 and 3,862,630 to Balamuth. Generally, however, the Balamuth device, as disclosed in those patents, does not coagulate and cut sufficiently fast, and lacks versatility in that it cannot be used to cut/coagulate without the clamp because access to the blade is blocked by the clamp, requires the blade to be replaced to change the blend of cutting versus coagulating, i.e., only one blade edge is available at any one time, and has a large tip which limits its usefulness as a tool for grasping and blunt dissecting.

DISCLOSURE OF THE INVENTION

Accordingly, the present invention provides a novel and improved ultrasonically-actuated surgical instrument for cutting/coagulating tissue, particularly loose and unsupported tissue, wherein the ultrasonic blade is employed in conjunction with a clamp for applying a compressive or biasing force to the tissue in a direction normal to the direction of vibration whereby faster coagulation and cutting of the tissue, with less attenuation of blade motion, are achieved. Further, the present invention provides the foregoing features, in one embodiment hereof, as a clamp coagulator accessory for a standard ultrasonic surgical instrument wherein the instrument may be particularly adapted for endoscopic surgery. A standard ultrasonic surgical instrument comprises essentially a generator which contains a power source for generating a 55,500 Hz electrical drive sinusoidal waveform and a handpiece containing preferably a piezoceramic transducer for converting such electrical signal into longitudinal mechanical vibration for coupling to a blade assembly. The clamp coagulator accessory adapts this standard ultrasonic unit for use in conjunction with a clamp assembly whereby tissue, particularly loose tissue, may be clamped between a clamping jaw and the blade for cutting and coagulating the tissue.

To accomplish the foregoing, there is provided, in one embodiment hereof, a handpiece housing the ultrasonic transducer, a nosecone or adapter for adapting the handpiece to receive the clamp coagulator accessory, and an elongated blade assembly comprised of a blade extender and a blade coupler carrying the blade and coupled to one end of the blade extender. The nosecone is threadedly secured to an end of the handpiece and the blade assembly is threaded onto the handpiece by a blade wrench, for example, of the type described and illustrated in U.S. Pat. Nos. 5,059,210 and 5,057,199, of common assignee herewith. The clamp coagulator accessory includes a clamp assembly comprised of a clamp jaw pivotally mounted on an end of a tube carried at its opposite end by a clamp activation mechanism, i.e., a scissors-like grip, and a clamp assembly mount for releasably connecting the clamp assembly to the handpiece to preclude relative longitudinal and rotational movement of the clamp accessory relative to the handpiece when the instrument is in use and to enable selected rotation of the handpiece and blade relative to the clamp assembly to orient a blade edge or a selected blade edge of a multi-edged blade in an operative position. As will be developed, the operative position of a blade edge may be in direct opposition to the clamp jaw when tissue clamping and cutting are desired or at another angular location or rotational orientation relative to the clamp jaw, e.g., facing 180° away from the clamp jaw, when tissue cutting and coagulation, or coagulation alone, are desired. The clamp assembly mount includes a locking lever and pad, the locking lever being pivotably movable between positions locking and unlocking the clamp coagulator accessory and the handpiece relative to one another. The scissors-like grip of the clamp activation mechanism includes discrete thumb and finger grips wherein one of the grips, e.g., the thumb grip, is coupled to a clamp jaw actuating rod extending through the tube to pivot the clamp jaw between clamp-open and clamp-closed positions relative to the blade. Hence, by squeezing the scissor-like grips, the clamp jaw is pivotable toward the clamp-closed position and into engagement with the blade. By displacing the grips oppositely, i.e., displacing the thumb grip away from the finger grip, the clamp jaw is positively pivotally displaced away from the blade into its clamp-open position.

Additionally, the clamp assembly is rotatable relative to the clamp assembly mount and the handpiece to rotationally orient a blade edge in operative position, e.g., in opposition to the clamp jaw or otherwise. Detents are provided to indicate to the user the proper rotationally oriented position of the blade with respect to the clamp jaw and to lock the blade in that position.

To apply the clamp coagulator accessory to the handpiece, the nosecone or adapter is screw-threaded on the end of the handpiece. One end of the blade assembly, specifically one end of the blade extender, is then inserted through the nosecone and screw-threaded to the end of the handpiece, whereby ultrasonic vibration may be transmitted from the transducer element in the handpiece along the blade extender to the blade at its opposite end. With the locking lever of the clamp assembly mount in an unlocked position, the clamp coagulator accessory receives the blade assembly through its proximal end, i.e., the blade assembly is received within and extends through the clamp assembly mount and the clamp assembly including its tube. A pin is received through a distal end portion of the tube to engage a flat and a radiussed portion of the blade coupler to enable relative longitudinal and rotational alignment of the blade and clamp jaw. Because the blades are attached to the handpiece by threaded joints and the blade designs are of different lengths, rotational and longitudinal alignment of the clamp accessory relative to the handpiece is necessary to overcome any rotational and longitudinal variations. When aligned, e.g., with one of the blade edges in lateral opposition to the clamping jaw at the end of the clamp assembly tube, the locking lever is closed to clamp the handpiece and clamp coagulator accessory to one another to preclude relative longitudinal and rotational movement of these parts.

The clamp assembly and the clamp assembly mount are secured one to the other against relative axial movement but are rotatable relative to one another between selected rotational positions. Thus, by rotating the assemblies relative to one another, a blade edge, or a selected blade edge of a multi-edged blade, can be rotated into selected operative detented position relative to the clamp jaw, i.e., in opposition to or rotationally misaligned relative to the clamp jaw, e.g., circumferentially spaced 180° from the clamp jaw.

In accordance with another aspect of the present invention, the blade may have one edge or multiple edges. In one embodiment, there is provided a blade having a narrow edge and a broad edge circumferentially spaced from the narrow edge. The blade and clamp are relatively rotatable about a longitudinal axis to locate one or the other of the blade edges in operative position, e.g., in opposition to the clamp jaw or circumferentially spaced therefrom. The different edges, with or without the clamp jaw, perform different functions, e.g., provide more or less cutting and coagulating action, depending on the tissue being cut and coagulated. When clamping tissue, a selected blade edge is rotated into opposition to the clamp jaw and the clamp jaw is pivoted to engage the tissue against the blade edge in a fully-clamped condition. Alternatively, a selected blade edge may be rotated to an operative position rotationally misaligned relative to a clamp jaw for purposes of cutting and coagulating tissue, or coagulating tissue without cutting, both without clamping. This selectivity allows the surgeon to create different tissue effects by different blade edge selection without replacing the blade or the entire instrument, e.g., a broad surface coagulates more than it cuts, while a narrow surface cuts faster but still coagulates. The broad-radiussed surface of the blade concentrates pressure when the tissue is clamped and, thus, substantial energy is delivered in the center of the contact zone, while still delivering energy to the edges of that zone. The radiussing also eliminates sharp edges at the border of the coagulation zone. Thus, accidental shearing during coagulation is avoided and thorough coaptive sealing of opposite walls of blood vessels is assured.

For thin tissue cutting, parallelism of the clamp jaw and blade edge is essential. To accomplish that with a multi-edged blade having broad and narrow edges, it is a feature of the present invention that the distance from the center of rotation of the blade to the narrow edge is greater than the distance to the broad edge. A groove is also formed along the length of the clamp jaw surface which mates with the narrow edge of the blade so that thin-tissue structures, such as adhesions, can be cut completely through with reliability because the groove aids the shearing action. The pad surface is serrated in a direction perpendicular to the axis of ultrasonic vibration. The longitudinal groove enables the narrow blade edge to contact the pad along the entire pad length despite those serrations, because the groove is as deep or deeper than the serrations. This also assures that thin structures can be cut through. This geometry also enables the pad surface of the jaw to lie parallel to whichever blade surface is used, despite the fact that the clamp jaw is pivotal. The clamp jaw rotation is thus stopped by the bottom of the groove of the clamp jaw surface when the narrow blade edge is selected and is stopped by the tips of the serrations on the clamp jaw surface when the broad blade edge is selected. Because those stops are in different planes, the two blade edges cannot both be parallel to the pad in the closed position of the clamp jaw without the different radial distances between the center of rotation of the blade and the respective edges of the blade.

The device of the present invention may be used in many different ways. For example, to clamp, coagulate and cut, the clamp jaw is opened and the desired blade edge is rotated into opposition to the clamp jaw. The instrument is then advanced so that the tissue enters the jaw between the clamp and blade and the grips are activated to close the clamp jaw, i.e., pivot the clamp jaw toward the blade edge. With ultrasonic power applied, the blade vibration couples to the tissue, causing coagulation and cutting of the tissue. Significantly, the tissue biasing or clamping force is in a direction normal to the longitudinal direction of vibration. The device may also be used for tissue grasping without the application of ultrasonic energy. Further, the device may be used for unclamped coagulating/cutting. That is, with the clamp jaw open, the desired blade edge may be rotated to a position unobstructed by the clamp jaw, e.g., facing away from the clamp jaw. When the instrument is advanced so that the side or end of the blade contacts the tissue, ultrasonic power may be applied, ultrasonically coupling the tissue and the blade, causing coagulation and cutting or coagulation alone. Still further, blunt dissection may be accomplished. With the clamp jaw closed, the clamp jaw and blade tip may be inserted between two tissue masses or planes. By opening the clamp jaw, the forces separate the tissue masses by tearing the bond between the masses.

Generally, the present ultrasonic surgical instrument clamps or biases tissue against a blade to improve the coupling of the ultrasonic energy to the tissue which enhances the cutting and coagulation action. It enables cutting and coagulating tissue which is loose or less supported, i.e., tissue which moves when only slight pressure is applied against it. By providing a clamping surface, pressing or biasing the tissue in a direction normal to the direction of vibration as opposed to parallel to the direction of vibration, the coagulation and cutting is faster with less applied power. The shearing action is also enhanced and blade motion or vibration attenuation is less when the clamping pressure or bias is normal to the vibratory direction of the blade. Further, a scissors-like jaw or pivotal clamp jaw enables the instrument to be used for grasping tissue and blunt tissue dissection in addition to cutting/coagulating with or without clamping. This versatility enables faster surgical procedures because it avoids the need to swap conventional instruments. Note particularly that the clamping action for cutting and coagulation can be used or a cutting or coagulating action, or both, without clamping, can be used without changing the blade or the position of the blade. Thus, at least one entire active edge of the blade is exposed and can be used directly on tissue without clamping. The capability of rotating the blade to bring additional blade edges into operative position, i.e., in opposition to the clamp or otherwise, by simply rotating a knob on the instrument enables the surgeon to create different tissue effects without replacing the blade or the entire instrument. Further, the clamp accessory is readily removable from the handpiece for cleaning and replacement.

In a preferred embodiment according to the present invention, there is provided ultrasonic surgical apparatus comprising a housing, an element carried by the housing for generating ultrasonic vibration, a surgical blade having an elongated edge carried by the housing and coupled to the element for receiving ultrasonic vibration therefrom for vibration in a longitudinal direction parallel to the blade edge, a clamp in opposition to the blade and along one side thereof for biasing tissue between the clamp and the blade for movement in a direction toward the blade and substantially normal to the longitudinal direction of vibration of the blade, and means for selectively displacing the clamp toward and away from the blade.

In a further preferred embodiment according to the present invention, there is provided ultrasonic surgical apparatus comprising a handpiece, an element carried by the handpiece for generating ultrasonic vibration, a surgical blade having an elongated edge carried by the handpiece and coupled to the element for receiving ultrasonic vibration therefrom for vibration in a longitudinal direction substantially parallel to the blade edge, and an accessory including a clamp assembly, means for releasably connecting the clamp assembly and the handpiece to one another, the clamp assembly including a clamp disposed in opposition to the blade and along one side thereof, when the accessory and the handpiece are connected to one another, for biasing tissue between the clamp and the blade for movement in a direction toward the blade and normal to the longitudinal direction of vibration of the blade together with means carried by the accessory for selectively displacing the clamp toward and away from the blade.

In a further preferred embodiment, there is provided an accessory for an ultrasonic surgical apparatus having a handpiece carrying an element for generating ultrasonic vibration and a blade having an elongated edge and connected to the element for receiving ultrasonic vibration from the element for vibration in a longitudinal direction parallel to the blade edge, comprising a clamp assembly including a clamp jaw carried for movement between clamp jaw open and clamp jaw closed positions, and a clamp jaw activating mechanism for moving the clamp jaw from the open position to the closed position. Means are carried by the accessory for releasably connecting the accessory and the handpiece to one another, the accessory, when connected to the handpiece, being configured to locate the clamp jaw in opposition to the blade and along one side thereof for biasing tissue between the clamp jaw and the blade for movement in a direction toward the blade and normal to the direction of vibration of the blade when the clamp jaw is moved toward the clamp jaw closed position.

In a still further preferred embodiment according to the present invention, there is provided ultrasonic surgical apparatus comprising a housing, an element carried by the housing for generating ultrasonic vibration, an elongated surgical blade carried by the housing and coupled to the element for receiving ultrasonic vibration therefrom for vibration in a longitudinal direction parallel to the blade, a clamp carried by the apparatus in opposition to a portion of the blade for biasing tissue between the clamp and the blade portion for movement in a direction toward the blade portion, the clamp having a clamping surface formed of compliant material and in opposition to the blade portion, and means for selectively displacing the clamp toward and away from the blade portion.

Accordingly, it is a primary object of the present invention to provide a novel and improved ultrasonic surgical instrument which provides effective cutting and coagulation of soft, particularly loose or unsupported, tissue and which instrument has the versatility to afford multiple functions in a single device, such as tissue clamping, grasping, blunt tissue dissection, cutting tissue with simultaneous coagulation and coagulation alone, without cutting.

BRIEF DESCRIPTION OF THE DRAWINGS

FIGS. 1a–1c are schematic illustrations of the assembly of a clamp coagulator accessory and an ultrasonic surgical instrument;

FIG. 3 is an enlarged fragmentary cross-sectional view of the distal end of the clamp coagulating accessory illustrating the cooperation of the ultrasonic surgical blade and a clamp jaw, the clamp jaw being illustrated in a jaw-open position;

FIG. 4 is a cross-sectional view thereof generally taken about on line 4—4 in FIG. 3;

FIG. 5 is an enlarged fragmentary longitudinal cross-sectional view of the accessory with the clamp jaw illustrated in a closed position;

FIGS. 8k–8o are side elevational views of additional forms of blades in conjunction with the clamp jaw;

FIGS. 9 and 10 are end elevational views of the blades illustrated in FIGS. 8k and 8l, respectively.

BEST MODE FOR CARRYING OUT THE INVENTION

Reference will now be made in detail to a present preferred embodiment of the invention, an example of which is illustrated in the accompanying drawings.

Figure 2:
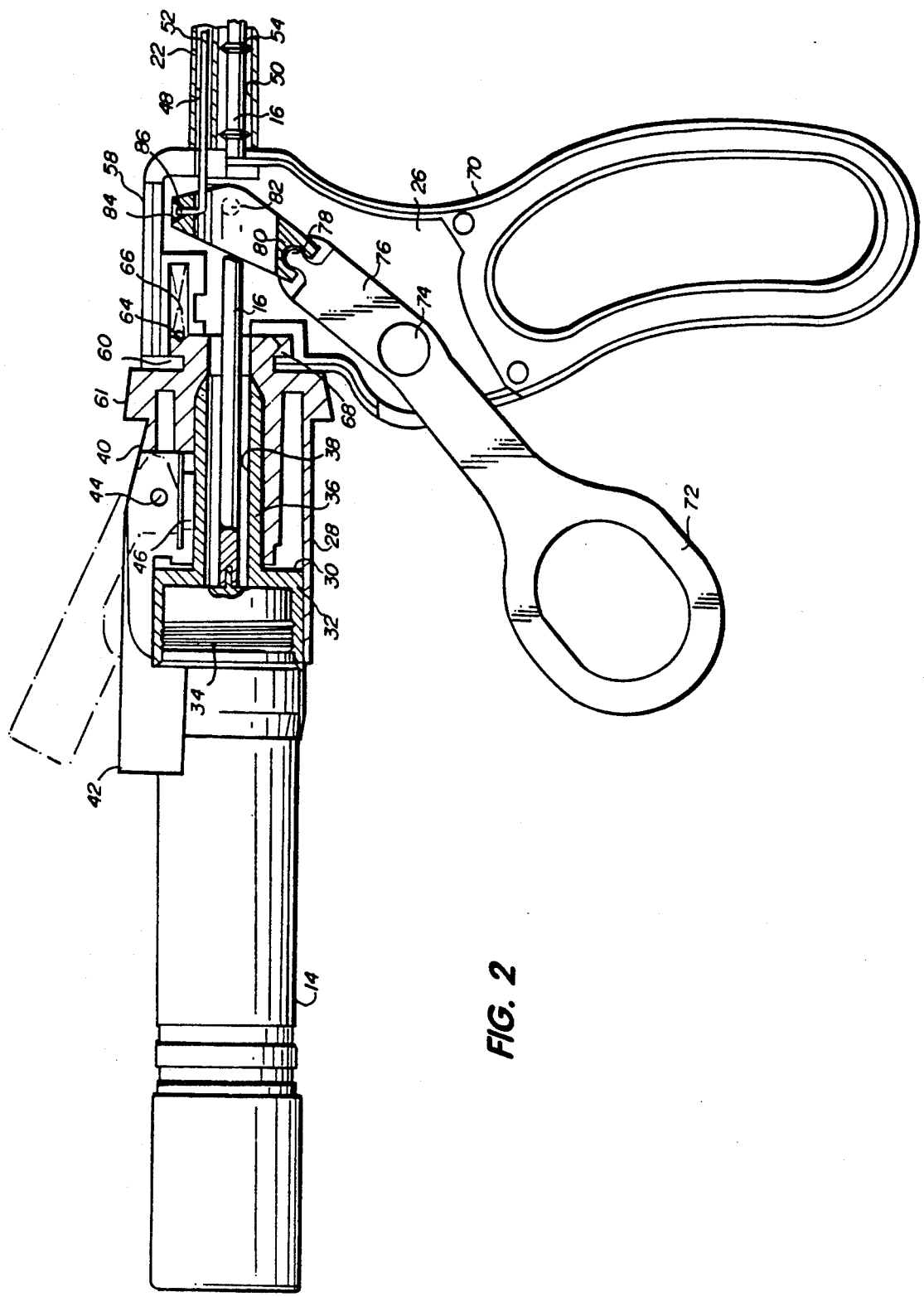
FIG. 2 is an enlarged fragmentary cross-sectional view illustrating the clamp coagulating accessory hereof secured to the handpiece of the ultrasonic instrument.

Referring now to FIGS. 1a–1c, there is illustrated an ultrasonic surgical apparatus constructed in accordance with the present invention and including an ultrasonic surgical instrument, generally designated 10, and a clamp coagulator accessory, generally designated 12. Ultrasonic instrument 10 comprises a housing or handpiece 14 housing a transducer, preferably a piezoeceramic transducer, for converting an electrical signal, for example, a 55,000 Hz sinusoidal waveform, into a mechanical longitudinal vibration. With reference to FIGS. 1a and 2, instrument 10 further includes a blade coupler extension 16 having a blade coupler 18 screw-threaded to the distal end of extension 16, blade coupler 18 carrying a blade 20. The proximal end of extension 16, as illustrated in FIG. 2, is screw-threaded onto a stud projecting from one end of handpiece 14 and connected to the transducer, whereby ultrasonic vibrations in a longitudinal direction are transmitted along extender 16 and blade coupler 18 to blade 20.

Clamp coagulator accessory 12 includes a clamp assembly comprised of an elongated tube 22 pivotally carrying a clamping jaw 24 at its distal end and a clamp jaw activation mechanism 26 at its proximal end. Accessory 12 also includes a clamp assembly mount 28 connected to the clamp assembly, as well as an adapter or nosecone 30. The nosecone 30 is illustrated in FIGS. 1 and 2 as attached, preferably by screw-threading, to the end of handpiece 14, the nosecone or adapter 30, however, comprising part of the clamp coagulator accessory for adapting the surgical instrument 10 for use with the clamp of accessory 12.

In general, it will be appreciated that the blade coupler 18 can be connected directly to handpiece 14 without the nosecone 30 and extender 16 and the ultrasonic instrument 10 may be used for cutting and coagulating in a conventional manner. The clamp coagulator accessory 12 may be disposed on the handpiece 14 with or without the extender 16, depending upon the desired length of the surgical apparatus, and may be provided in different lengths for different surgical purposes. For endoscopic, particularly laparoscopic use, the extender 16 is applied to the handpiece 14 and the accessory 12 includes the elongated tube 22 housing the extender 16. Thus, in the illustrated form, the clamp coagulator accessory is particularly adapted for laparoscopic use, although it will be appreciated that the clamp accessory may be provided the handpiece or housing 14 for other surgical uses.

As illustrated, particularly in FIG. 2, the nosecone 30 of accessory 12 includes an internally threaded cup-shaped housing 32 for threaded engagement with external threads 34 formed on the distal end of the handpiece 14. Nosecone 30 also includes an axially extending sleeve 36 having a central bore 38. It will be appreciated that extender 16 extends through bore 38 for threaded connection with handpiece 14. Clamp assembly mount 28 includes a generally cylindrical fitting 40 having an axial bore for receiving the sleeve 36 of nosecone 30. A lever 42 is pivotally mounted at 44 to fitting 40, lever 42 compressing a pad 46 for engagement along the outer surface of sleeve 36 to secure accessory 12 and the handpiece 10 one to the other against longitudinal and rotational movement. Lever 42 operates as an over-center toggle and is thus pivotal between accessory mounting and demounting positions relative to handpiece 10, as illustrated by the full and dashed lines in FIG. 2.

As further illustrated in FIG. 2, tube 22 has a pair of axial bores 48 and 50. Bore 48 carries an actuating rod 52 for actuating clamp jaw 24, as described in the ensuing description. When the accessory 12 is mounted to handpiece 14, bore 50 receives the extender 16. As illustrated, extender 16 carrying a plurality of longitudinally spaced rings, preferably formed of silicone, located at the node points of extender 16 to minimize or eliminate dissipation of the ultrasonic longitudinal vibration of the extender 16 by contact with tube 22. The tube 22 is suitably fixed to the clamp activation mechanism 26.

Clamp activation mechanism 26 includes a housing 58 having an annular flange 60 secured behind a corresponding annular flange 62 formed on the fitting 40. The cooperating flanges 60 and 62 enable the clamp assembly and the clamp assembly mount 28 to rotate relative to one another while maintaining a fixed axial position relative to one another. The center of rotation lies coincident with the central axis of extender 16 when the accessory 12 is applied to the instrument 10. Housing 58 includes a ball detent 64 biased by a spring 66 into one of a plurality of circumferentially spaced recesses formed on the end face of fitting 40. Consequently, fitting 40 and the clamp assembly may be rotated relative to one another into selected detented positions. A finger control ring or knob 61 is carried by, and preferably formed integrally with, fitting 40 to facilitate relative rotation between the clamp assembly and the clamp assembly mount.

Mechanism 26 includes scissors-like gripping handles or grips for pivoting the clamp jaw between open and closed positions. Particularly, mechanism 26 includes a fixed finger handle or grip 70 and a thumb handle or grip 72 pivoted to housing 58 by pin 74. Thumb grip 72 is also fixed to a link 76 having a projecting knob 78 received in a corresponding recess along the lower side of a generally annular ring 80. Ring 80 is mounted in housing 58 for pivotal movement about a generally transverse axis intersecting the longitudinal axis of the combined accessory and handpiece 14. Suitable pins 82 are provided for pivotally mounting the ring 80 to housing 58 along its lateral sides. The upper portion of ring 80 includes an aperture 84 for receiving an upwardly bent end 86 of the actuator rod 52.

It will be appreciated from the foregoing and a review of drawing FIGS. 2 and 5 that pivoting thumb grip 72 toward finger grip 70 about 74 causes link 76 to pivot ring 80 in a clockwise direction, as illustrated in FIG. 2, with a substantial mechanical advantage. As will be appreciated from the following description, rotation of ring 80 in a clockwise direction displaces actuator rod 52 forwardly along tube 22 to pivot clamp jaw 24 into its closed position. Movement of thumb grip 72 in the opposite direction rotates ring 80 about pivot pins 82 in a counterclockwise direction, as illustrated in FIG. 2, to displace actuator rod 52 in the opposite direction, i.e., rearwardly, and hence pivot the clamp jaw 24 into its clamp open position. This clamp jaw movement is indicated upon comparison of FIGS. 3 and 5.

Clamp jaw 24 is illustrated in FIG. 3 in a clamp open position and is pivotally attached to the actuator rod 52 adjacent the base of the clamp jaw. The clamp jaw is pivotally carried in a recess on the end of tube 22 by a pin 90. It will be seen that, by advancing actuator rod 52 toward jaw 24, jaw 24 is pivoted in a clockwise direction about pivot pin 90 into the clamp closed position of FIG. 5 with the clamp pad 110, described hereinafter, bearing against the blade 18. Retracting movement of actuator rod 52 pivots the clamp jaw 24 in a generally counterclockwise direction into the clamp open position illustrated in FIG. 3.

Because the blade coupler is screw-threaded to the extender 16 or to the handpiece 14 and blade couplers and extenders of different sizes are provided, an alignment guide is provided for obtaining rotational and longitudinal alignment of the accessory and the instrument when the accessory is applied to the instrument to account for variations in the threaded dimensions and to align the blade relative to clamp jaw 24. In one form of the alignment guide, there is provided a pin 98 which is receivable in a laterally extending aperture 100 in tube 22. When the blade coupler 18 is formed, it includes an enlarged diameter portion 102 having radiussed edges 104 and flats 106 extending from edges 104 formed along opposite sides thereof. By inserting the pin 98 through tube 22 and inserting the accessory over the extender 16 and blade coupler 18, instrument 10 and accessory 12 can be manipulated such that rotational movement is prohibited by the engagement of the pin along one of flats 106 and longitudinal closing movement of the two parts is arrested by the engagement of the pin along a radiussed edge 104.

Figure 6:
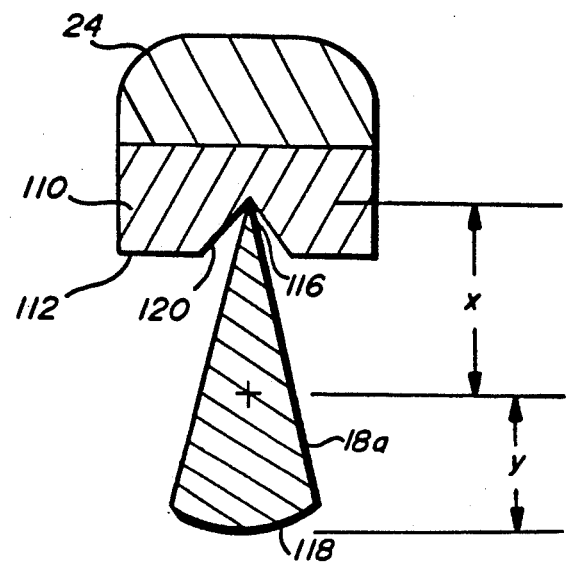
FIGS. 6 and 7 are schematic enlarged end elevational views of the cooperation between the clamp jaw and a multi-edged blade, the blade being illustrated in 180° apart orientations relative to the clamp jaw, respectively.
Figure 7:
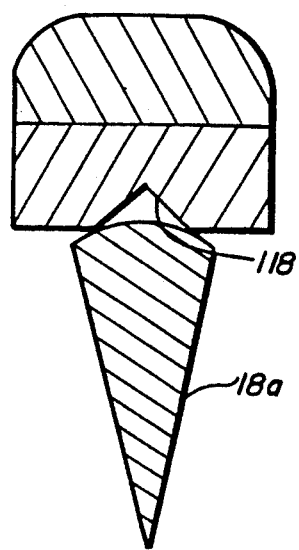

Referring now to FIGS. 3, 6 and 7, the clamp jaw 24 mounts a pad 110 for squeezing the tissue between the blade 18 and clamp jaw 24 against the side of the blade 18 to use the shearing action of the vibration to enhance tissue cutting/coagulating effects. Pad 110 is preferably formed of a polymeric or other compliant material and engages the blade edge when pivoted to its fully closed position. The use of compliant pad material prevents loud and annoying audible noise which would occur if an ultrasonic blade were to contact a non-compliant (e.g., metallic) pad. Preferably, the pad is formed of a material having a low coefficient of friction but which has substantial rigidity to provide tissue-grasping capability, such as Teflon. The pad 110 may be mounted to the clamp jaw 24 by an adhesive or mechanical fastener.

Serrations 112 are formed in the clamping surface of pad 110 and extend perpendicular to the blade axis to allow tissue to be grasped, manipulated, coagulated and cut without slipping from between the jaw and blade. While the jaw 24 is pivoted within the recess at the end of tube 22, the sides of the tube 22 are tapered to minimize obstruction of vision of the blade and jaw by the tube consistent with the need to provide mechanical support for the clamp jaw. Additionally, it will be seen that the leading end of the tube 22 provides a tissue stop to prevent the tissue from entering the clamp coagulator jaw beyond the ultrasonically active region of the blade. For reasons discussed hereinafter, the pad 110 also has a longitudinally extending groove 118 (FIGS. 6 and 7), preferably a V-shaped groove, along its length and recessed among the serrations 112 to an extent at least as deep as, and preferably deeper than, the serrations 112.

Referring now to FIGS. 6 and 7, and in accordance with another aspect of the present invention, there is provided a blade having multiple blade edges which, when coupled with the ability to relatively rotate the blade and clamp jaw, affords the surgeon the availability of more than one blade characteristic without replacing the blade and the use of multiple blade edges with or without the clamp. For example, a preferred blade design may comprise a generally triangular-shaped blade 18a in cross-section with two discrete edges, i.e., a narrow edge 116 to concentrate the ultrasonic energy enabling fast cutting/coagulating of unsupported tissue with clamping, and a broad edge or face 118 to create a wider zone of coaptive coagulation. As illustrated, the preferred shape of the broad face is a convex curve in a plane perpendicular to the direction of vibration. This concentrates the ultrasonic energy in the center of the clamp jaw area and reduces the risk of shear cutting uncoagulated vessels at the blade edge.

With the substantially V-shaped groove 120 formed in the pad surface of the clamp jaw 24, the narrow edge 116 may be received in the apex of the groove. This enables the narrow blade edge 116 to squeeze tissue with some shearing force in addition to the compressive clamping force. The groove 120 is preferably as deep or deeper than the depth of serrations so that the narrow blade edge makes full pad contact along its length when the clamp jaw is closed. Both the shearing action and the full-length contact aid in cutting thin tissue.

To accommodate the different edges of the illustrated blade 18a, the blade geometry is such that the narrow edge 116 is further from the axis of rotation of the blade than the broad edge 118 by an amount equal to the depth of the longitudinal groove. Thus X, the distance of edge 116 from the rotational axis is greater than Y, the distance of edge 118 from the rotational axis, as illustrated, in FIG. 6 and by a distance corresponding to the depth of groove 120. This geometry allows the pad surface to be parallel to and in contact with whichever blade edge is in use, notwithstanding that the clamp jaw closure is a pivotal action. Thus, the clamp jaw rotation is stopped by the bottom of the groove 120 when the narrow edge 116 is selected for use and is stopped by the tips of the pad serrations 112 adjacent the groove when the broad edge 118 is in use. Because these stops lie in different planes, the two blade edges would not otherwise be parallel to the pad 110 except for the variation in distance between the axis of rotation and the respective narrow and broad edges of the blade.

To assemble the instrument 10 and accessory 12, the nosecone 30 is screw-threaded onto the end of handpiece 14. The extender 16, with attached blade coupler 18, are then screw-threaded into the male stud projecting from the end face of handpiece 14. Because the blade is attached to the handpiece by a threaded joint, the angular orientation of the blade relative to the handpiece is a variable. Because the accessory 12 is also oriented relative to the handpiece, the initial angular orientation of the blade relative to the clamp jaw is also a variable. Further, the longitudinal position of the blade tip relative to the clamp can also vary due to the requirement to manufacture each blade assembly so that its length is an integer multiple of one-half the wavelength. Thus, the assembled blade must be oriented rotationally and longitudinally to align with the clamp jaw. To accomplish this, the alignment pin 98 is passed through the aperture 100 in the tube 22 prior to attachment of the accessory and handpiece to one another. With the pin in place, the accessory is telescoped over the blade coupler and extender such that the blade coupler and extender are received in the bore 50 of tube 22. By rotationally manipulating the accessory and instrument, the pin will engage along a flat 106 of blade coupler 18. With further telescoping movement of the accessory and instrument, the blade coupler radiussed edge 104 will engage against the pin 98. When this occurs, the accessory and handpiece are longitudinally and rotationally aligned, with the result that the blade and clamp are aligned. Locking lever 42 is then pivoted to clamp the accessory 12 to handpiece 14 to maintain that alignment. The alignment pin 98 is then removed. It will be appreciated that in the clamped condition, the clamp assembly mount and clamp assembly are detented in a selected rotational position relative to one another.

In using the device, with the accessory applied to the instrument as previously described, it will be appreciated that the clamp can be used to coagulate and cut with ultrasonic energy applied, can be used to grasp tissue without application of ultrasonic energy, can be used to coagulate/cut with the jaw open and tissue unclamped, can be used to probe or manipulate tissue without application of ultrasonic energy, and can be used, with the clamp jaw closed, for blunt dissection. For example, when the clamp is used for coagulation/cutting, the clamp jaw is opened by opening the finger and thumb grips 70 and 72, respectively. The desired blade edge is then rotated to face the clamp jaw surface. To accomplish that, the knob 61 can be rotated while holding the clamp assembly to thereby rotate the handpiece 14, extender 16, blade coupler 18 and blade 20 relative to the clamp assembly including tube 22 and clamp jaw 24 into a position locating the selected blade edge in opposition to the clamp jaw. The detent provided by the spring-biased ball 64 maintains this selected rotary alignment.

The apparatus may then be advanced so that tissue enters the space between the clamp and blade. The scissors-like grips are activated to close the jaw and ultrasonic power is applied. The longitudinal blade vibration relative to the clamp jaw couples to the tissue, causing coagulation and tissue cutting. Tissue grasping can also be performed by following the above procedure but without application of ultrasonic energy to the instrument. To coagulate and cut in an unclamped condition, and with the clamp jaw open, the handpiece and mount can be rotated relative to the clamp assembly to locate a desired blade edge in an operative condition, i.e., at a circumferential location other than in opposition to the clamp jaw. When the device is advanced so that the blade contacts the tissue, and ultrasonic power is applied, the blade vibration couples to the tissue, causing coagulation or both coagulation and tissue cutting. For blunt dissection, the clamp jaw may be closed and the clamp and blade tip inserted between two tissue masses or planes. By opening the clamp jaw, the tissue masses may be forced apart.

Figure 8A:
FIGS. 8a–8j are schematic cross-sectional views through various forms of blade and clamp jaws in accordance with the present invention.
Figure 8B:
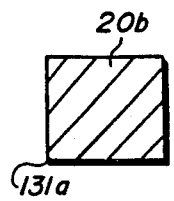
Figure 8C:

Referring now to drawing FIGS. 8a through 8o, there is illustrated a number of different blade and jaw designs for use with the ultrasonic surgical apparatus of the present invention. In FIG. 8a, the blade 20a is generally rectangular in cross-section having broad surfaces 127 and narrow or medium-sized edges 129. The broad or narrow or medium edge surfaces can be brought into alignment with the clamp jaw or into other operative positions by rotation through 90° to provide a choice of coagulation widths. In FIG. 8b, four broad surfaces are provided, with a blade design which is substantially square in cross-section. Again, these surfaces can be brought into operative position by rotating the blade relative to the clamp jaw through 90°. Alternatively, a narrow edge 131a can be brought into operative position by rotating the blade 45°, if faster cutting is desired. FIG. 8c illustrates a blade 20c having a generally triangular-shaped cross-section. The blade edges at the juncture of the sides of the triangular-shaped blade provide narrow cutting edges while the broad surfaces therebetween afford coagulating surface. Thus, the broad and narrow edges can be brought into operative position by rotating the blade 20c through 60°.

Figure 8D:
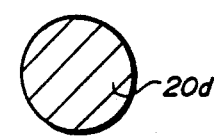
Figure 8E:
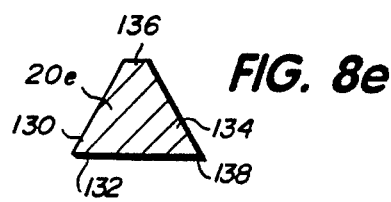

In FIG. 8d, a blade 20d is provided which is circular in cross-section. This blade, of course, does not require rotational alignment vis-a-vis the clamp jaw. The blade illustrated in FIG. 8e has a truncated triangular configuration, with three relatively broad surfaces 130, 132 and 134, a medium surface 136 and narrow cutting edges 138. As in the prior embodiment, rotation of this blade through 60° will locate those edges in sequence in an operative position to allow a wide variety of coagulation and cutting blends.

Figure 8F:
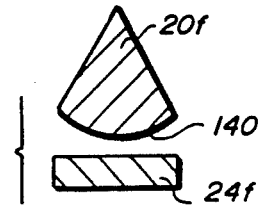
Figure 8G:
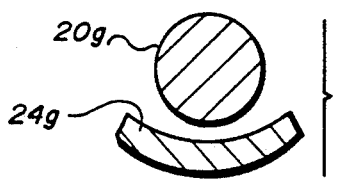
Figure 8G:
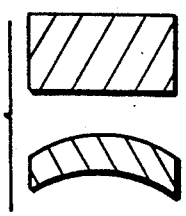
Figure 8H:
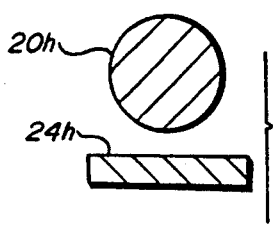

In FIG. 8f, a blade 20f, similar to that disclosed in FIGS. 6 and 7, is disposed in opposition to a flat jaw 24f. The broad convex surface 140 has the capacity to deliver more energy to the center of the contact zone along the flat jaw 24f. In FIG. 8g, a blade 20g has a circular cross-section and is generally concentric with the arcuate surface of the jaw 24g. This combination affords an even pressure between the blade and jaw and provides uniform coagulation across the blade face. Alternatively, in FIG. 8g', the blade surface may be made flat and the damp surface convex to achieve the same gradient of ultrasonic energy, to achieve thorough coagulation while cutting the tissue. In FIG. 8h, the blade 20h is circular in cross-section and the jaw 24h is flat, enabling a concentration of pressure, essentially along the juncture line between the blade and jaw.

Figure 8I:
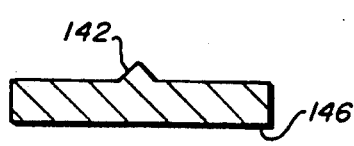
Figure 8J:
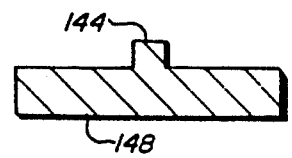

In FIGS. 8i and 8j, the blade is essentially rectilinear, with a projection to one side of the blade. In FIG. 8i, the projection is triangular-shaped, while in FIG. 8j, the projection 144 is generally rectangular in shape. Thus, the bottom broad surfaces at 146 and 148 may be rotated into operative position for purposes of coagulating. The broad surfaces with the projections or ridges 142 and 144, when brought into operative position opposite the clamp jaw, create a wide coagulation zone and cut through the tissue with the ridges. Additionally, the medium surfaces along the side edges of these blades can be employed for cutting and coagulating. Referring to FIG. 8k, the blade 20k is generally circular in cross-section and has a circular tip 150. This narrow tip is used for dissecting. In FIG. 8l, the blade 20l has a generally teardrop shape in cross-section, with a ridge 152 projecting from its distal end. This blade tip similarly as the blade in FIG. 8k, may be used for dissecting. In FIG. 8m, there is provided a blade 20m having a generally circular cross-section, with a conical tip 154 for point coagulation/cutting. In FIG. 8n, the blade 20n is generally circular in cross-section, having a flat, wide and relatively narrow tip 156 for effecting improved coagulation. The blade 20o of FIG. 8o is generally circular in cross-section and has a bulbous tip 158, likewise for improving coagulation. Blade tip 158 also minimizes the potential for cutting tissue accidentally as coagulation is performed.

Figure 8P:
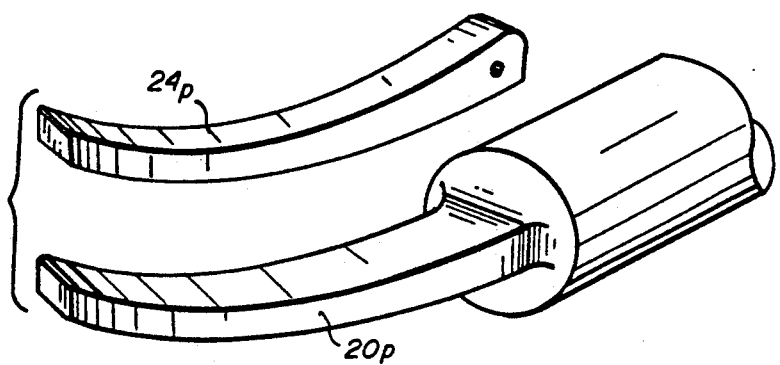
FIGS. 8p–8s are perspective views of further forms of blades.
Figure 8Q:
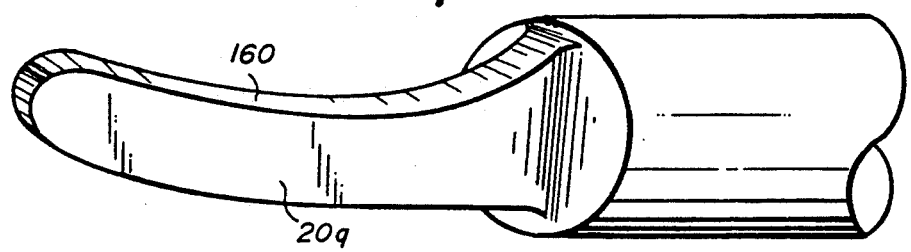
Figure 8R:
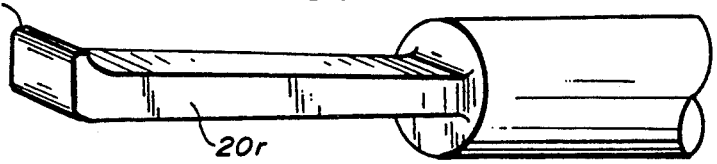
Figure 8S:
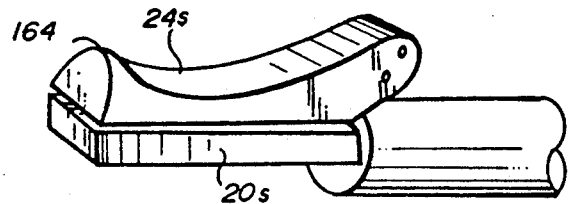

In the blade and jaw combination illustrated in FIG. 8p, the blade 24p is generally rectilinear in cross-section and arcuate in a direction toward a similarly arcuate jaw 24p. This curved tip facilitates treatment of tissue at awkward angles of approach. Jaw 24p a generally rectilinear cross-section. The blade 20q, illustrated in FIG. 8q, is generally long and narrow, with a concave recessed side 160, also advantageous for different angles of approach. The blade 20r of FIG. 8r is generally rectilinear in cross-section, having a hooked blade tip 162, which facilitates grasping and pulling tissue. In FIG. 8s, the blade 20s is flat and generally rectilinear in cross-section. In this form, the jaw 24s has a hooked tip 164. The hooked tip jaw affords better gripping action during dissection.

While the invention has been described with respect to what is presently regarded as the most practical embodiments thereof, it will be understood by those of ordinary skill in the art that various alterations and modifications may be made which nevertheless remain within the scope of the invention as defined by the claims which follow.

What is claimed is:

1. Ultrasonic surgical apparatus comprising:
a housing;
an ultrasonic element carried by said housing for generating ultrasonic vibration;
a surgical blade having an elongated edge carried by said housing and coupled to said ultrasonic element for receiving ultrasonic vibration therefrom for vibration in a longitudinal direction parallel to said blade edge;
a clamp carried by said apparatus in opposition to said blade and along one side thereof for biasing tissue between the clamp and the blade for movement in a direction toward the blade and substantially normal to the longitudinal direction of vibration of said blade; and
means for selectively displacing said clamp toward and away from said blade.

2. Apparatus according to claim 1 wherein said means for selectively displacing said clamp further includes means for pivoting said clamp toward and away from said blade.

3. Apparatus according to claim 1 wherein said blade and said clamp are mounted for movement relative to one another about an axis extending parallel to the longitudinal direction of vibration of said blade to locate said blade edge in an operative position relative to said clamp, and means carried by said apparatus for effecting relative movement of said blade and said clamp to locate said blade edge in said operative position.

4. Apparatus according to claim 1 wherein said blade has at least two elongated discrete edges spaced circumferentially from one another about an axis of the blade extending generally parallel to the longitudinal direction of vibration, said blade and said clamp being mounted for movement relative to one another to selectively locate one of said blade edges in an operative position relative to said clamp, and means carried by said apparatus for effecting relative movement of said blade and said clamp to located said one of said blade edges in said operative cutting position.

5. Apparatus according to claim 4 including means cooperable between said housing and said clamp for rotating said blade about an axis generally parallel to the direction of vibration for selectively locating said one of said blade edges in said operative position.

6. Apparatus according to claim 5 wherein said one of said selected blade edges in said operative position thereof lies in opposition to said clamp.

7. Apparatus according to claim 4 wherein said one of said blade edges in said operative position thereof lies in opposition to said clamp, said blade edges comprising respective first and second edges configured to provide respectively different cutting and coagulating characteristics in cooperation with said clamp when in said operative position.

8. Apparatus according to claim 7 including means for relatively rotating said blade and said clamp about an axis generally parallel to the longitudinal direction of vibration for selectively locating one of said first and second blade edges in said operative position, the axis of rotation being located such that the radial distance of said first blade edge from said axis is greater than the radial distance of said second blade edge from said axis, said clamp having a clamping surface with an elongated recess for receiving said first edge of said blade when the clamp lies in a closed position and surface portions for receiving said second edge of said blade when the clamp lies in the closed position, enabling the blade edges to lie generally parallel to said clamping surface when said first and second blade edges lie in said position, respectively, with said clamp in its closed position.

9. Apparatus according to claim 8 wherein said clamping surface includes a plurality of serrations spaced from one another and extending in a direction normal to the axis of rotation, said recess extending within said serrations in a direction parallel to the axis of rotation when said clamp lies in its closed position.

10. Apparatus according to claim 1 wherein said clamp includes a clamping surface formed of a compliant material.

11. Apparatus according to claim 1 wherein said clamp includes a clamping surface formed of a polymeric compliant material, said clamping surface including a groove in said surface extending in a longitudinal direction generally parallel to and for receiving said elongated blade edge.

12. Apparatus according to claim 1 wherein said clamp includes a clamping surface formed of a polymeric compliant material, said clamping surface including a plurality of serrations spaced from one another and extending in a direction normal to the longitudinal direction of said elongated blade edge.

13. Apparatus according to claim 1 wherein said clamp includes a clamping surface formed of a compliant material, said clamping surface including a plurality of serrations spaced from one another and extending in a direction normal to the longitudinal direction of said elongated blade edge, said clamping surface also including a groove in said serrated clamping surface extending in a longitudinal direction generally parallel to and for receiving said elongated blade edge, said groove having a depth at least as great as said serrations.

14. Apparatus according to claim 1 adapted for laparoscopic use, and including an extender interconnecting said ultrasonic element and said blade, a tube carried by said apparatus and extending about and radially spaced from said extender, means for isolating the ultrasonic vibration transmitted from said ultrasonic element along said extender to said blade from said tube including means engageable between said tube and said extender at at least one vibratory node along said extender whereby dissipation of ultrasonic vibration along said extender by engagement with said tube is substantially minimized or precluded, said displacing means including means extending along said tube and operable from said housing for displacing said clamp toward and away from said blade.

15. Apparatus according to claim 1 wherein said displacing means includes scissors-like grips with at least one grip movable toward and away from another of said grips to displace said clamp toward and away from said blade.

16. Ultrasonic surgical apparatus comprising:
a handpiece;
an ultrasonic element carried by said handpiece for generating ultrasonic vibration;
a surgical blade having an elongated edge carried by said handpiece and coupled to said ultrasonic element for receiving ultrasonic vibration therefrom for vibration in a longitudinal direction substantially parallel to said blade edge;
an accessory including a clamp assembly, means for releasably connecting said clamp assembly and said handpiece to one another, said clamp assembly including a clamp disposed in opposition to said blade and along one side thereof, when said accessory and said handpiece are connected to one another, for biasing tissue between the clamp and the blade for movement in a direction toward the blade and normal to the longitudinal direction of vibration of said blade; and
means carried by said accessory for selectively displacing said clamp toward and away from said blade.

17. Apparatus according to claim 16 wherein said means selectively displacing said clamp further includes means for pivoting said clamp toward and away from said blade.

18. Apparatus according to claim 17 wherein said blade has at least two elongated discrete edges spaced circumferentially from one another about an axis of the blade extending generally parallel to the longitudinal direction of vibration, said blade and said clamp being mounted for movement relative to one another to selectively locate one of said blade edges in an operative position relative to said clamp, and means carried by said accessory for relatively moving said blade and said clamp to locate said one of said blade edges in said operative position.

19. Apparatus according to claim 18 including means cooperable between said clamp assembly and said connecting means for selectively rotating said blade and said clamp about an axis generally parallel to the direction of vibration for locating said one of said blade edges in said operative position.

20. Apparatus according to claim 19 wherein said operative position of said blade edges is in opposition to said clamp.

21. Apparatus according to claim 18 wherein said operative position of said blade edges is in opposition to said clamp, said blade edges comprising respective first and second edges for cooperation with said clamp to provide respectively different cutting and coagulating characteristics.

22. Apparatus according to claim 21 including means carried by said accessory for relatively rotating said blade and said clamp about an axis generally parallel to the direction of vibration for selectively locating one of said first and second blade edges in said operative position, the axis of rotation being located such that the radial distance of said first blade edge from said axis is greater than the radial distance of said second blade edge from said axis, said clamp having a clamping surface with an elongated recess for receiving said first blade edge when said clamp lies in a closed position and surface portions for receiving said second blade edge when said clamp lies in the closed position, enabling the blade edges to lie generally parallel to said clamping surface when said one of said blade edges lies in said operative position.

23. Apparatus according to claim 22 wherein said clamping surface includes a plurality of serrations spaced from one another in a direction normal to the axis of rotation and said recess extends within said serrations in a direction parallel to the axis of rotation when said clamp lies in its closed position.

24. Apparatus according to claim 17 adapted for laparoscopic use, and including an extender interconnecting said ultrasonic element and said blade, a tube carried by said accessory and extending about and radially spaced from said extender, means for isolating the ultrasonic vibration transmitted from said ultrasonic element along said extender to said blade from said tube including means engageable between said tube and said extender at at least one vibratory node along said extender whereby dissipation of ultrasonic vibration along said extender by engagement with said tube is substantially minimized or precluded, said displacing means including means extending along said tube and operable from said housing for displacing said clamp toward and away from said blade.

25. Apparatus according to claim 16 wherein said blade and said clamp are mounted for movement relative to one another about an axis extending parallel to the longitudinal direction of vibration of said blade to locate said blade edge in an operative position relative to said clamp, and means carried by said apparatus for effecting relative movement of said blade and said clamp to locate said blade edges in said operative position.

26. Apparatus according to claim 16 wherein said clamp includes a clamping surface formed of a compliant material.

27. Apparatus according to claim 16 wherein said clamp includes a clamping surface formed of a polymeric compliant material, said clamping surface including a groove in said surface extending in a longitudinal direction generally parallel to and for receiving said elongated blade edge.

28. Apparatus according to claim 16 wherein said clamp includes a clamping surface formed of a polymeric compliant material, said clamping surface including a plurality of serrations spaced from one another and extending in a direction normal to the longitudinal direction of said elongated blade edge.

29. Apparatus according to claim 16 wherein said clamp includes a clamping surface formed of a compliant material, said clamping surface including a plurality of serrations spaced from one another and extending in a direction normal to the longitudinal direction of said elongated blade edge, said clamping surface also including a groove in said serrated clamping surface extending in a longitudinal direction generally parallel to and for receiving said elongated blade edge, said groove having a depth at least as great as said serrations.

30. Apparatus according to claim 16 including means cooperable between said accessory and said blade for rotationally aligning said blade edge and said clamp in a predetermined orientation relative to one another when said accessory and said handpiece are initially connected to one another.

31. Apparatus according to claim 16 including means cooperable between said accessory and said blade for longitudinally aligning said blade edge and said clamp in a predetermined orientation relative to one another when said accessory and said handpiece are initially connected to one another.

32. Apparatus according to claim 16 including means cooperable between said accessory and said blade for rotationally and longitudinally aligning said blade edge and said clamp in a predetermined orientation relative to one another when said accessory and said handpiece are initially connected to one another.

33. An accessory for an ultrasonic surgical apparatus having a handpiece carrying an ultrasonic element for generating ultrasonic vibration and a blade having an elongated edge and connected to said ultrasonic element for receiving ultrasonic vibration from said ultrasonic element for vibration in a longitudinal direction parallel to the blade edge comprising:
 a clamp assembly including a clamp jaw carried for movement between clamp jaw open and clamp jaw closed positions, and a clamp jaw activating means for moving said clamp jaw from said open position to said closed position;
 means carried by said accessory for releasably connecting said accessory and the handpiece to one another, said accessory, when connected to the handpiece, being configured to locate said clamp jaw in opposition to the blade and along one side thereof for biasing tissue between said clamp jaw and the blade for movement in a direction toward the blade and normal to the direction of vibration of said blade when said clamp jaw is moved toward said clamp jaw closed position.

34. An accessory according to claim 33 wherein said clamp jaw is carried by said clamp assembly for pivotal movement between said clamp jaw open and clamp jaw closed position.

35. An accessory according to claim 33 including a clamp assembly mount carrying said accessory connecting means, and means for connecting said clamp assembly and said clamp assembly mount to one another enabling relative rotation thereof about an axis to rotationally orient said clamp jaw and the blade relative to one another when the accessory and handpiece are connected one to the other.

36. An accessory according to claim 35 wherein said connecting means between said clamp assembly and said clamp assembly mount includes means for detenting said clamp assembly and said clamp assembly mount in selected rotational orientations relative to one another.

37. An accessory according to claim 33 wherein said clamp jaw activating means includes a pair of scissors-like grips carried by said clamp assembly with one of said grips being movable toward and away from the other of said grips and means interconnecting said one grip and said clamp jaw to move said clamp jaw toward said clamp jaw closed position in response to movement of said one grip toward said other grip.

38. An accessory according to claim 37 wherein said clamp assembly includes an elongated tube having an axis and a distal end, said clamp jaw being pivotally carried by said tube adjacent said distal end thereof for movement between said clamp jaw open position wherein said clamp jaw forms an angle with the axis of said tube and said clamp jaw closed position wherein said clamp jaw lies generally parallel to said axis, said interconnecting means including an actuating rod extending along said tube and connected to said clamp jaw.

39. An accessory according to claim 37 wherein said clamp assembly includes an elongated tube having an axis and a distal end, said clamp jaw being pivotally carried by said tube adjacent said distal end thereof for movement between said clamp jaw open position wherein said clamp jaw forms an angle with the axis of said tube and said clamp jaw closed position wherein said clamp jaw lies generally parallel to said axis, said interconnecting means including an actuating rod extending along said tube and connected to said clamp jaw, said tube having an elongated passage for receiving an extender carried by the handpiece when the accessory and the handpiece are connected to one another, said interconnecting means including a generally ring-shaped member pivotally carried by said clamp assembly and coupled to said one grip on one side of the pivotal axis thereof and to said actuating rod on an opposite side of the pivotal axis, the opening through said ring-shaped member lying in alignment with said passage wherein the extension shaft is receivable through said ring and into said passage when said accessory and the handpiece are connected to one another.

40. An accessory according to claim 33 wherein said clamp assembly includes an elongated tube having an axis and a distal end, said clamp jaw being pivotally carried by said tube adjacent said distal end thereof for movement between said clamp jaw open position wherein said clamp jaw forms an angle with the axis of said tube and said clamp jaw closed position wherein said clamp jaw lies generally parallel to said axis.

41. An accessory according to claim 33 wherein said clamp includes a clamping surface formed of a compliant material.

42. Ultrasonic surgical apparatus comprising:
 a housing;
 an ultrasonic element carried by said housing for generating ultrasonic vibration;
 an elongated surgical blade carried by said housing and coupled to said ultrasonic element for receiving ultrasonic vibration therefrom for vibration in a longitudinal direction parallel to said blade;
 a clamp carried by said apparatus in opposition to a portion of said blade for biasing tissue between the clamp and the blade portion for movement in a direction toward the blade portion, said clamp having a clamping surface formed of compliant material and in opposition to said blade portion; and means for selectively displacing said clamp toward and away from said blade portion.

* * * * *

REEXAMINATION CERTIFICATE (3355th)

United States Patent [19]

Davison et al.

[11] B1 5,322,055
[45] Certificate Issued Oct. 14, 1997

[54] CLAMP COAGULATOR/CUTTING SYSTEM FOR ULTRASONIC SURGICAL INSTRUMENTS

[75] Inventors: Thomas W. Davison, North Attleboro; Stephen DiMatteo, Seekonk, both of Mass.; Paul Smith, West Warwick, R.I.; Gary Whipple, South Attleboro, Mass.

[73] Assignee: Ultracision Inc., Smithfield, R.I.

Reexamination Request:
No. 90/004,208, Apr. 9, 1996

Reexamination Certificate for:
Patent No.: 5,322,055
Issued: Jun. 21, 1994
Appl. No.: 8,809
Filed: Jan. 27, 1993

[51] Int. Cl.$^6$ ............................................. A61B 17/32
[52] U.S. Cl. ........................... 601/2; 604/22; 606/169; 606/170; 606/171
[58] Field of Search ................................. 606/169–171

[56] References Cited

U.S. PATENT DOCUMENTS

| | | | |
|---|---|---|---|
| 2,845,072 | 7/1958 | Shafer | 128/303.14 |
| 3,053,124 | 9/1962 | Balamuth et al. | |
| 3,636,943 | 1/1972 | Balamuth | 128/24 |
| 3,657,056 | 4/1972 | Winston et al. | 156/580.2 |
| 3,792,701 | 2/1974 | Kloz et al. | 128/7 |
| 4,375,961 | 3/1983 | Brooks | 433/4 |
| 4,655,216 | 4/1987 | Tischer | |
| 4,723,545 | 2/1988 | Nixon et al. | 128/305 |
| 4,825,865 | 5/1989 | Zelman | 128/303.1 |
| 4,832,683 | 5/1989 | Idemoto et al. | 604/22 |
| 5,167,725 | 12/1992 | Clark et al. | 428/680 |
| 5,201,759 | 4/1993 | Ferzli | 606/170 |
| 5,263,957 | 11/1993 | Davison | 606/171 |
| 5,324,299 | 6/1994 | Davison et al. | 606/167 |

FOREIGN PATENT DOCUMENTS

| | | |
|---|---|---|
| 2 355 521 | 2/1978 | France . |
| 2032501 | 1/1972 | Germany . |
| 7705947 | 2/1977 | Germany . |
| 61-128954 | 6/1986 | Japan . |
| 232948 | 9/1989 | Japan . |
| 854366 | 3/1981 | U.S.S.R. . |

*Primary Examiner*—Ruth S. Smith

[57] ABSTRACT

An ultrasonic surgical apparatus includes a surgical instrument having a handpiece with a transducer for converting an electrical signal into longitudinal vibratory motion of a blade connected to the handpiece and an accessory releasably connected to the handpiece to enable clamping of tissue against the vibrating blade to afford improved coagulating and cutting of tissue. Scissors-like grips actuate a pivoted clamp jaw along one side of the ultrasonically vibrating blade to compress and bias tissue against the blade in a direction normal to the direction of longitudinal vibratory movement. The clamp jaw and blade are rotatable relative to one another to align a selected blade edge of a multi-edged blade with the clamp jaw for cutting and coagulating while clamping or circumferentially spacing a selected blade edge from the clamp jaw for cutting and coagulating without clamping.

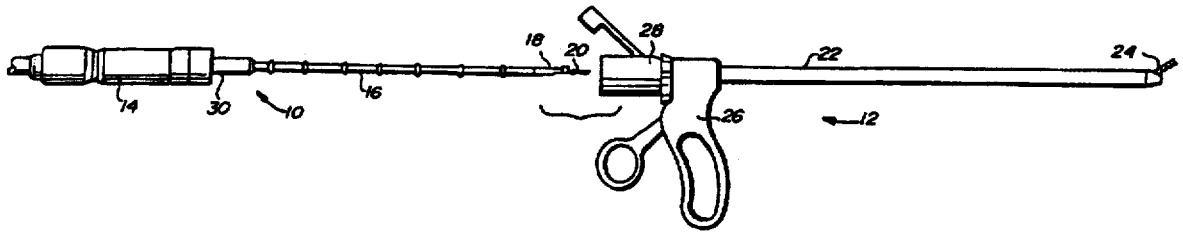

B1 5,322,055

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 2, 10, 15–17, 26, 31 and 42 is confirmed.

Claim 41 is cancelled.

Claims 3, 4, 11–14, 18, 24, 25, 27–30, 32, 33, 35 and 38–40 are determined to be patentable as amended.

Claims 5–9, 19–23, 34, 36 and 37, dependent on an amended claim, are determined to be patentable.

New claims 43–52 are added and determined to be patentable.

3. [Apparatus according to claim 1] *Ultrasonic surgical apparatus comprising:*
   *a housing;*
   *an ultrasonic element carried by said housing for generating ultrasonic vibration;*
   *a surgical blade having an elongated edge carried by said housing and coupled to said ultrasonic element for receiving ultrasonic vibration therefrom for vibration in a longitudinal direction parallel to said blade edge;*
   *a clamp carried by said apparatus in opposition to said blade and along one side thereof for biasing tissue between the clamp and the blade for movement in a direction toward the blade and substantially normal to the longitudinal direction of vibration of said blade* wherein said blade and said clamp are mounted for movement relative to one another about an axis extending parallel to the longitudinal direction of vibration of said blade to locate said blade edge in an operative position relative to said clamp, and means carried by said apparatus for effecting relative movement of said blade and said clamp to locate said blade edge in said operative position; *and*
   *means for selectively displacing said clamp toward and away from said blade.*

4. [Apparatus according to claim 1] *Ultrasonic surgical apparatus comprising:*
   *a housing;*
   *an ultrasonic element carried by said housing for generating ultrasonic vibration;*
   *a surgical blade having an elongated edge carried by said housing and coupled to said ultrasonic element for receiving ultrasonic vibration therefrom for vibration in a longitudinal direction parallel to said blade edge* wherein said blade has at least two elongated discrete edges spaced circumferentially from one another about an axis of the blade extending generally parallel to the longitudinal direction of vibration;
   *a clamp carried by said apparatus in opposition to said blade and along one side thereof for biasing tissue between the clamp and the blade for movement in a direction toward the blade and substantially normal to the longitudinal direction of vibration of said blade,* said blade and said clamp being mounted for movement relative to one another to selectively locate one of said blade edges in an operative position relative to said clamp, and means carried by said apparatus for effecting relative movement of said blade and said clamp to locate[d] said one of said blade edges in said operative cutting position; *and*
   *means for selectively displacing said clamp toward and away from said blade.*

11. [Apparatus according to claim 1] *Ultrasonic surgical apparatus comprising:*
    *a housing;*
    *an ultrasonic element carried by said housing for generating ultrasonic vibration;*
    *a surgical blade having an elongated edge carried by said housing and coupled to said ultrasonic element for receiving ultrasonic vibration therefrom for vibration in a longitudinal direction parallel to said blade edge;*
    *a clamp carried by said apparatus in opposition to said blade and along one side thereof for biasing tissue between the clamp and the blade for movement in a direction toward the blade and substantially normal to the longitudinal direction of vibration of said blade* wherein said clamp includes a clamping surface formed of a polymeric compliant material, said clamping surface including a groove in said surface extending in a longitudinal direction generally parallel to and for receiving said elongated blade edge; *and*
    *means for selectively displacing said clamp toward and away from said blade.*

12. [Apparatus according to claim 1] *Ultrasonic surgical apparatus comprising:*
    *a housing;*
    *an ultrasonic element carried by said housing for generating ultrasonic vibration;*
    *a surgical blade having an elongated edge carried by said housing and coupled to said ultrasonic element for receiving ultrasonic vibration therefrom for vibration in a longitudinal direction parallel to said blade edge;*
    *a clamp carried by said apparatus in opposition to said blade and along one side thereof for biasing tissue between the clamp and the blade for movement in a direction toward the blade and substantially normal to the longitudinal direction of vibration of said blade* wherein said clamp includes a clamping surface formed of a polymeric compliant material, said clamping surface including a plurality of serrations spaced from one another and extending in a direction normal to the longitudinal direction of said elongated blade edge; *and*
    *means for selectively displacing said clamp toward and away from said blade.*

13. [Apparatus according to claim 1] *Ultrasonic surgical apparatus comprising:*
    *a housing;*
    *an ultrasonic element carried by said housing for generating ultrasonic vibration;*
    *a surgical blade having an elongated edge carried by said housing and coupled to said ultrasonic element for receiving ultrasonic vibration therefrom for vibration in a longitudinal direction parallel to said blade edge;*
    *a clamp carried by said apparatus in opposition to said blade and along one side thereof for biasing tissue* between the clamp and the blade for movement in a direction toward the blade and substantially normal to the longitudinal direction of vibration of said blade wherein said clamp includes a clamping surface formed of a compliant material, said clamping surface including a plurality of serrations spaced from one another and extending in a direction normal to the longitudinal direction of said elongated blade edge, said clamping surface also including a groove in said serrated clamping surface extending in a longitudinal direction generally parallel to and for receiving said elongated blade edge, said groove having a depth at least as great as said serrations; and means for selectively displacing said clamp toward and away from said blade.

14. [Apparatus according to claim 1] *Ultrasonic surgical apparatus* adapted for laparoscopic use, [and including] comprising:

a housing;

an ultrasonic element carried by said housing for generating ultrasonic vibration;

a surgical blade having an elongated edge carried by said housing and coupled to said ultrasonic element for receiving ultrasonic vibration therefrom for vibration in a longitudinal direction parallel to said blade edge;

a clamp carried by said apparatus in opposition to said blade and along one side thereof for biasing tissue between the clamp and the blade for movement in a direction toward the blade and substantially normal to the longitudinal direction of vibration of said blade;

means for selectively displacing said clamp toward and away from said blade;

an extender interconnecting said ultrasonic element and said blade[.];

a tube carried by said apparatus and extending about and radially spaced from said extender[.]; *and* means for isolating the ultrasonic vibration transmitted from said ultrasonic element along said extender to said blade from said tube including means engageable between said tube and said extender at least one vibratory node along said extender whereby dissipation of ultrasonic vibration along said extender by engagement with said tube is substantially minimized or precluded, said displacing means including means extending along said tube and operable from said housing for displacing said clamp toward and away from said blade.

18. [Apparatus according to claim 17] *Ultrasonic surgical apparatus comprising:* a handpiece;

an ultrasonic element carried by said handpiece for generating ultrasonic vibration;

a surgical blade having an elongated edge carried by said handpiece and coupled to said ultrasonic element for receiving ultrasonic vibration therefrom for vibration in a longitudinal direction substantially parallel to said blade edge wherein said blade has at least two elongated discrete edges spaced circumferentially from one another about an axis of the blade extending generally parallel to the longitudinal direction of vibration;

an accessory including a clamp assembly, means for releasably connecting said clamp assembly and said handpiece to one another, said clamp assembly including a clamp disposed in opposition to said blade and along one side thereof, when said accessory and said handpiece are connected to one another, for biasing tissue between the clamp and the blade for movement in a direction toward the blade and normal to the longitudinal direction of vibration of said blade, said blade and said clamp being mounted for movement relative to one another to selectively locate one of said blade edges in an operative position relative to said clamp[, and];

means carried by said accessory for relatively moving said blade and said clamp to locate said one of said blade edges in said operative position; *and* means carried by said accessory for selectively displacing said clamp toward and away from said blade including means for pivoting said clamp toward and away from said blade.

24. [Apparatus according to claim 17] *Ultrasonic surgical apparatus* adapted for laparoscopic use[, and including] comprising:

a handpiece;

an ultrasonic element carried by said handpiece for generating ultrasonic vibration;

a surgical blade having an elongated edge carried by said handpiece and coupled to said ultrasonic element for receiving ultrasonic vibration therefrom for vibration in a longitudinal direction substantially parallel to said blade edge;

an accessory including a clamp assembly, means for releasably connecting said clamp assembly and said handpiece to one another, said clamp assembly including a clamp disposed in opposition to said blade and along one side thereof, when said accessory and said handpiece are connected to one another, for biasing tissue between the clamp and the blade for movement in a direction toward the blade and normal to the longitudinal direction of vibration of said blade;

means carried by said accessory for selectively displacing said clamp toward and away from said blade including means for pivoting said clamp toward and away from said blade;

an extender interconnecting said ultrasonic element and said blade[.];

a tube carried by said accessory and extending about and radially spaced from said extender[.]; *and* means for isolating the ultrasonic vibration transmitted from said ultrasonic element along said extender to said blade from said tube including means engageable between said tube and said extender at least one vibratory node along said extender whereby dissipation of ultrasonic vibration along said extender by engagement with said tube is substantially minimized or precluded, said displacing means including means extending along said tube and operable from said housing for displacing said clamp toward and away from said blade.

25. [Apparatus according to claim 16] *Ultrasonic surgical apparatus comprising:* a handpiece;

an ultrasonic element carried by said handpiece for generating ultrasonic vibration;

a surgical blade having an elongated edge carried by said handpiece and coupled to said ultrasonic element for receiving ultrasonic vibration therefrom for vibration in a longitudinal direction substantially parallel to said blade edge;

an accessory including a clamp assembly, means for releasably connecting said clamp assembly and said handpiece to one another, said clamp assembly including a clamp disposed in opposition to said blade and along one side thereof, when said accessory and said handpiece are connected to one another, for biasing tissue between the clamp and the blade for movement in a direction toward the blade and normal to the longitudinal direction of vibration of said blade wherein said blade and said clamp are mounted for movement relative to one another about an axis extending parallel to the longitudinal direction of vibration of said blade to locate said blade edge in an operative position relative to said clamp[, and];

means carried by said apparatus for effecting relative movement of said blade and said clamp to locate said blade edges in said operative position; and means carried by said accessory for selectively displacing said clamp toward and away from said blade.

27. [Apparatus according to claim 16] *Ultrasonic surgical apparatus comprising:*

*a handpiece;*

*an ultrasonic element carried by said handpiece for generating ultrasonic vibration;*

*a surgical blade having an elongated edge carried by said handpiece and coupled to said ultrasonic element for receiving ultrasonic vibration therefrom for vibration in a longitudinal direction substantially parallel to said blade edge;*

*an accessory including a clamp assembly, means for releasably connecting said clamp assembly and said handpiece to one another, said clamp assembly including a clamp disposed in opposition to said blade and along one side thereof, when said accessory and said handpiece are connected to one another, for biasing tissue between the clamp and the blade for movement in a direction toward the blade and normal to the longitudinal direction of vibration of said blade* wherein said clamp includes a clamping surface formed of a polymeric compliant material, said clamping surface including a groove in said surface extending in a longitudinal direction generally parallel to and for receiving said elongated blade edge; *and*

*means carried by said accessory for selectively displacing said clamp toward and away from said blade.*

28. [Apparatus according to claim 16] *Ultrasonic surgical apparatus comprising:*

*a handpiece;*

*an ultrasonic element carried by said handpiece for generating ultrasonic vibration;*

*a surgical blade having an elongated edge carried by said handpiece and coupled to said ultrasonic element for receiving ultrasonic vibration therefrom for vibration in a longitudinal direction substantially parallel to said blade edge;*

*an accessory including a clamp assembly, means for releasably connecting said clamp assembly and said handpiece to one another, said clamp assembly including a clamp disposed in opposition to said blade and along one side thereof, when said accessory and said handpiece are connected to one another, for biasing tissue between the clamp and the blade for movement in a direction toward the blade and normal to the longitudinal direction of vibration of said blade* wherein said clamp includes a clamping surface formed of a polymeric compliant material, said clamping surface including a plurality of serrations spaced from one another and extending in a direction normal to the longitudinal direction of said elongated blade edge; *and*

*means carried by said accessory for selectively displacing said clamp toward and away from said blade.*

29. [Apparatus according to claim 16] *Ultrasonic surgical apparatus comprising:*

*a handpiece;*

*an ultrasonic element carried by said handpiece for generating ultrasonic vibration;*

*a surgical blade having an elongated edge carried by said handpiece and coupled to said ultrasonic element for receiving ultrasonic vibration therefrom for vibration in a longitudinal direction substantially parallel to said blade edge;*

*an accessory including a clamp assembly, means for releasably connecting said clamp assembly and said handpiece to one another, said clamp assembly including a clamp disposed in opposition to said blade and along one side thereof, when said accessory and said handpiece are connected to one another, for biasing tissue between the clamp and the blade for movement in a direction toward the blade and normal to the longitudinal direction of vibration of said blade* wherein said clamp includes a clamping surface formed of a compliant material, said clamping surface including a plurality of serrations spaced from one another and extending in a direction normal to the longitudinal direction of said elongated blade edge, said clamping surface also including a groove in said serrated clamping surface extending in a longitudinal direction generally parallel to and for receiving said elongated blade edge, said groove having a depth at least as great as said serrations; *and*

*means carried by said accessory for selectively displacing said clamp toward and away from said blade.*

30. [Apparatus according to claim 16 including] *Ultrasonic surgical apparatus comprising:*

*a handpiece;*

*an ultrasonic element carried by said handpiece for generating ultrasonic vibration;*

*a surgical blade having an elongated edge carried by said handpiece and coupled to said ultrasonic element for receiving ultrasonic vibration therefrom for vibration in a longitudinal direction substantially parallel to said blade edge;*

*an accessory including a clamp assembly, means for releasably connecting said clamp assembly and said handpiece to one another, said clamp assembly including a clamp disposed in opposition to said blade and along one side thereof, when said accessory and said handpiece are connected to one another, for biasing tissue between the clamp and the blade for movement in a direction towarad the blade and normal to the longitudinal direction of vibration of said blade;* means cooperable between said accessory and said blade for rotationally aligning said blade edge and said clamp in a predetermined orientation relative to one another when said accessory and said handpiece are initially connected to one another; and

*means carried by said accessory for selectively displacing said clamp toward and away from said blade.*

32. [Apparatus according to claim 16 including] *Ultrasonic surgical apparatus comprising:*

*a handpiece;*

*an ultrasonic element carried by said handpiece for generating ultrasonic vibration;*

*a surgical blade having an elongated edge carried by said handpiece and coupled to said ultrasonic element for* receiving ultrasonic vibration therefrom for vibration in a longitudinal direction substantially parallel to said blade edge;

an accessory including a clamp assembly, means for releasably connecting said clamp assembly and said handpiece to one another, said clamp assembly including a clamp disposed in opposition to said blade and along one side thereof, when said accessory and said handpiece are connected to one another, for biasing tissue between the clamp and the blade for movement in a direction toward the blade and normal to the longitudinal direction of vibration of said blade means cooperable between said accessory and said blade for rotationally and longitudinally aligning said blade edge and said clamp in a predetermined orientation relative to one another when said accessory and said handpiece are initially connected to one another; and means carried by said accessory for selectively displacing said clamp toward and away from said blade.

33. An accessory for an ultrasonic surgical apparatus having a handpiece carrying an ultrasonic element for generating ultrasonic vibration and a blade having an elongated edge and connected to said ultrasonic element for receiving ultrasonic vibration from said ultrasonic element for vibration in a longitudinal direction parallel to the blade edge comprising:

a clamp assembly including a clamp jaw carried for movement between clamp jaw open and clamp jaw closed positions, and a clamp jaw activating means for moving said clamp jaw from said open position to said closed position *wherein said clamp includes a clamping surface formed of a compliant material*;

means carried by said accessory for releasably connecting said accessory and the handpiece to one another, said accessory, when connected to the handpiece, being configured to locate said clamp jaw in opposition to the blade and along one side thereof for biasing tissue between said clamp jaw and the blade for movement in a direction toward the blade and normal to the direction of vibration of said blade when said clamp jaw is moved toward said clamp jaw closed position.

35. [An accessory according to claim 33 including] *An accessory for an ultrasonic surgical apparatus having a handpiece carrying an ultrasonic element for generating ultrasonic vibration and a blade having an elongated edge and connected to said ultrasonic element for receiving ultrasonic vibration from said ultrasonic element for vibration in a longitudinal direction parallel to the blade edge comprising:*

*a clamp assembly including a clamp jaw carried for movement between clamp jaw open and clamp jaw closed positions, and a clamp jaw activating means for moving said clamp jaw from said open position to said closed position;*

*means carried by said accessory for releasably connecting said accessory and the handpiece to one another, said accessory, when connected to the handpiece, being configured to locate said clamp jaw in opposition to the blade and along one side thereof for biasing tissue between said clamp jaw and the blade for movement in a direction toward the blade and normal to the direction of vibration of said blade when said clamp jaw is moved toward said clamp jaw closed position;* a clamp assembly mount carrying said accessory connecting means[,]; and means for connecting said clamp assembly and said clamp assembly mount to one another enabling relative rotation thereof about an axis to rotationally orient said clamp jaw and the blade relataive to one another when the accessory and handpiece are connected one to the other.

38. [An accessory according to claim 37 wherein said clamp assembly includes] *An accessory for an ultrasonic surgical apparatus having a handpiece carrying an ultrasonic element for generating ultrasonic vibration and a blade having an elongated edge and connected to said ultrasonic element for receiving ultrasonic vibration from said ultrasonic element for vibration in a longitudinal direction parallel to the blade edge comprising:*

*a clamp assembly including a clamp jaw carried for movement between clamp jaw open and clamp jaw closed positions, and* an elongated tube having an axis and a distal end, said clamp jaw being pivotally carried by said tube adjacent said distal end thereof for movement between said clamp jaw open position wherein said clamp jaw forms an angle with the axis of said tube and said clamp jaw closed position wherein said clamp jaw lies generally parallel to said axis *and a clamp jaw activating means for moving said clamp jaw from said open position to said closed position wherein said clamp jaw activating means includes a pair of scissors-like grips carried by said clamp assembly with one of said grips being movable toward and away from the other of said grips and means interconnecting said one grip and said clamp jaw to move said clamp jaw toward said clamp jaw closed position in response to movement of said one grip toward said other grip*, said interconnecting means including an actuating rod extending along said tube and connected to said clamp jaw; and

*means carried by said accessory for releasably connecting said accessory and the handpiece to one another, said accessory, when connected to the handpiece, being configured to locate said clamp jaw in opposition to the blade and along one side thereof for biasing tissue between said clamp jaw and the blade for movement in a direction toward the blade and normal to the direction of vibration of said blade when said clamp jaw is moved toward said clamp jaw closed position.*

39. [An accessory according to claim 37 wherein said clamp assembly includes] *An accessory for an ultrasonic surgical apparatus having a handpiece carrying an ultrasonic element for generating ultrasonic vibration and a blade having an elongated edge and connected to said ultrasonic element for receiving ultrasonic vibration from said ultrasonic element for vibration in a longitudinal direction parallel to the blade edge comprising:*

*a clamp assembly including a clamp jaw carried for movement between clamp jaw open and clamp jaw closed positions, and* an elongated tube having an axis and a distal end, said clamp jaw being pivotally carried by said tube adjacent said distal end thereof for movement between said clamp jaw open position wherein said clamp jaw forms an angle with the axis of said tube and said clamp jaw closed position wherein said clamp jaw lies generally parallel to said axis *and a clamp jaw activating means for moving said clamp jaw from said open position to said closed position wherein said clamp jaw activating means includes a pair of scissors-like grips carried by said clamp assembly with one of said grips being movable toward and away from the other of said grips and means interconnecting said one grip and said clamp jaw to move said clamp jaw toward said clamp jaw closed position in response to move-* ment of said one grip toward said other grip, said interconnecting means including an actuating rod extending along said tube and connected to said clamp jaw, said tube having an elongated passage for receiving an extender carried by the handpiece when the accessory and the handpiece are connected to one another, said interconnecting means including a generally ring-shaped member pivotally carried by said clamp assembly and coupled to said one grip on one side of the pivotal axis thereof and to said actuating rod on an opposite side of the pivotal axis, the opening through said ring-shaped member lying in alignment with said passage wherein the extension shaft is receivable through said ring and into said passage when said accessory and the handpiece are connected to one another; and means carried by said accessory for releasably connecting said accessory and the handpiece to one another, said accessory, when connected to the handpiece, being configured to locate said clamp jaw in opposition to the blade and along one side thereof for biasing tissue between said clamp jaw and the blade for movement in a direction toward the blade and normal to the direction of vibration of said blade when said clamp jaw is moved toward said clamp jaw closed position.

40. [An accessory according to claim 33 wherein said clamp assembly includes] *An accessory for an ultrasonic surgical apparatus having a handpiece carrying an ultrasonic element for generating ultrasonic vibration and a blade having an elongated edge and connected to said ultrasonic element for receving ultrasonic vibration from said ultrasonic element for vibration in a longitudinal direction parallel to the blade edge comprising:*

*a clamp assembly including a clamp jaw carried for movement between clamp jaw open and clamp jaw closed positions, and* said clamp assembly includes an elongated tube having an axis and a distal end, said clamp jaw being pivotally carried by said tube adjacent said distal end thereof for movement between said clamp jaw open position wherein said clamp jaw forms an angle with the axis of said tube and said clamp jaw closed position wherein said clamp jaw lies generally parallel to said axis *and a clamp jaw activating means for moving said clamp jaw from said open position to said closed position;* means carried by said accessory for releasably connecting said accessory and the handpiece to one another, said accessory, when connected to the handpiece, being configured to locate said clamp jaw in opposition to the blade and along one side thereof for biasing tissue between said clamp jaw and the blade for movement in a direction toward the blade and normal to the direction of vibration of said blade when said clamp jaw is moved toward said clamp jaw closed position.

*43. Apparatus according to any one of claims 1–32 or 42 inclusive, wherein said blade is curved.*

*44. Apparatus according to any one of claims 1–32 inclusive, wherein said edge is arcuate.*

*45. Apparatus according to any one of claims 10, 26, or 42 wherein said compliant material comprises a polymeric material.*

*46. Apparatus according to any one of claims 10, 26, or 42 wherein said compliant material comprises a substantially rigid material having a low coefficient of friction.*

*47. Apparatus according to any one of claims 10, 26, or 42 wherein said compliant material comprises Teflon.*

*48. An accessory according to any one of claims 33–40 inclusive, wherein said blade is curved.*

*49. An accessory according to any one of claims 33–40 inclusive, wherein said edge is arcuate.*

*50. An accessory according to any one of claims 33–40 inclusive, wherein said compliant material comprises a polymeric material.*

*51. An accessory according to any one of claims 33–40 inclusive, wherein said compliant material comprises a substantially rigid material having a low coefficient of friction.*

*52. An accessory according to any one of claims 33–40 inclusive, wherein said compliant material comprises Teflon.*

* * * * *